United States Patent
Yi et al.

(10) Patent No.: US 10,519,184 B2
(45) Date of Patent: Dec. 31, 2019

(54) 5-FORMYLCYTOSINE SPECIFIC CHEMICAL LABELING METHOD AND RELATED APPLICATIONS

(71) Applicant: PEKING UNIVERSITY, Beijing (CN)

(72) Inventors: Chengqi Yi, Beijing (CN); Bo Xia, Beijing (CN); Ankun Zhou, Beijing (CN)

(73) Assignee: PEKING UNIVERSITY (CN)

( * ) Notice: Subject to any disclaimer, the term of this patent is extended or adjusted under 35 U.S.C. 154(b) by 664 days.

(21) Appl. No.: 15/023,881

(22) PCT Filed: Sep. 26, 2014

(86) PCT No.: PCT/CN2014/087479
§ 371 (c)(1),
(2) Date: Mar. 22, 2016

(87) PCT Pub. No.: WO2015/043493
PCT Pub. Date: Apr. 2, 2015

(65) Prior Publication Data
US 2016/0362438 A1 Dec. 15, 2016

(30) Foreign Application Priority Data
Sep. 27, 2013 (CN) .......................... 2013 1 0452515

(51) Int. Cl.
*C07H 19/06* (2006.01)
*C07H 1/00* (2006.01)
(Continued)

(52) U.S. Cl.
CPC ............... *C07H 19/06* (2013.01); *C07H 1/00* (2013.01); *C12Q 1/6858* (2013.01); *C12Q 1/6869* (2013.01)

(58) Field of Classification Search
CPC .................................................. C07H 19/06
(Continued)

(56) References Cited

U.S. PATENT DOCUMENTS

2016/0362438 A1 12/2016 Yi et al.

FOREIGN PATENT DOCUMENTS

| CN | 104311618 | 1/2015 |
|---|---|---|
| JP | 2012092240 | 5/2012 |

(Continued)

OTHER PUBLICATIONS

Tandem Knoevenagel-[3+2] Cycloaddition-Elimination Reactions: One-Pot Synthesis of 4,5-Disubstituted 1,2,3-(NH)-Triazoles; Thanasekaran Ponpandian et al; Tetrahedron Letters 53 (2012) 59-63; 6 pages.

(Continued)

*Primary Examiner* — Jezia Riley
(74) *Attorney, Agent, or Firm* — Mark E. Bandy; Rankin, Hill & Clark LLP

(57) ABSTRACT

The present invention relates to a 5-formylcytosine specific chemical labeling method and related applications in aspects such as sequencing, detection, imaging, and diagnosis. In the method, a condensation reaction occurs between an active methylene group in an active methylene compound containing a side-chain reactive group and an aldehyde group in 5-formylcytosine or a 1-substituted derivative of 5-formylcytosine, and at the same time an intramolecular reaction occurs between the side-chain reactive group of the active methylene compound and a 4-amino group of cytosine to implement ring closing. By means of the 5-formylcytosine specific chemical labeling method and related compounds of the present invention, detection of the content of 5-formylcytosine in nucleic acid molecules, and specific concentration of 5-formylcytosine-containing nucleic acid samples, and analysis of sequence distribution information of 5-formylcytosine and/or single-base resolution sequence information in nucleic acid molecules and the like may be implemented. The present invention provides various effective research methods in the research fields of epigenetics and nucleic acid biochemistry.

20 Claims, 10 Drawing Sheets

Specification includes a Sequence Listing.

(51) Int. Cl.
*C12Q 1/6858* (2018.01)
*C12Q 1/6869* (2018.01)

(58) Field of Classification Search
USPC .......................................................... 435/6.12
See application file for complete search history.

(56) References Cited

FOREIGN PATENT DOCUMENTS

| WO | WO2013017853 A2 | 2/2013 |
| WO | WO2013138644 A2 | 9/2013 |

OTHER PUBLICATIONS

Quantitative Sequencing of 5-Methylcytosine and 5-Hydroxymethylcytosine at Single-Base Resolution; Booth et al; May 18, 2012; vol. 336; 5 pg.

Genome-wide distribution of 5-formylcytosine in embryonic stem cells is associated with transcription and depends on thymine DNA glycosylase; Raiber et al; Genome Biology 2012; 13:R69; 11 pg.

Generation and replication-dependent dilution of 5fC and 5caC during mouse preimplantation development; Azusa Inoue et al; Cell Research (2011) 21 :1670-1676; 7 pages.

Bisultite-free, base-resolution analysis of 5-formylcytosine at the genome scale; Bo Xia et al; Nature Methods vol. 12 No. 11; Nov. 1, 2015; 7 pages.

Selective Chemical Labelling of 5-Formylcytosine in DNA by Fluorescent Dyes; Jianlin Hu et al; Chem. Eur. J. 2013.19, 5836-5840; 5 pages.

AID-Driven Deletion Causes Immunoglobulin Heavy Chain Locus Suicide Recombination in B Cells; Sophie Péron et al; www.sciencemag.org; vol. 336; May 18, 2012; 4 pages.

Takara, Mighty Amp, DNA Polymerase Ver. 3, Code No. R076A (11 pages).

Shen et al.; Genome-wide Analysis Reveals TET- and TDG-Dependent 5-Methylcytosine Oxidation Dynamics; Cell 153, 692-706, Apr. 25, 2013 (25 pages).

Chun-Xiao Song et al; Selective chemical labeling reveals the genome-wide distribution of 5-hydroxymethylcytosine; Dec. 12, 2010; Nature America, Inc.; 8 pages.

EpiTect® Bisulfite Handbook; Dec. 2014; www.qiagen.com; 48 pages.

A | 5'-AGATC^(s)GTAT-3'
Reaction raw material
Molecular weight: 2765.5
m/z^(ob): 2763.5

B | 5'-AGATC^(s)GTAT-3'
reacted with ethyl acetoacetate
Molecular weight: 2831.9
m/z^(ob): 2829.8

C | 5'-AGATC^(s)GTAT-3'
reacted with methyl acetoacetate
Molecular weight: 2831.9
m/z^(ob): 2829.5

D | 5'-AGATC^(s)GTAT-3'
reacted with malononitrile
Molecular weight: 2813.9
m/z^(ob): 2812.5

E | 5'-AGATC^(s)GTAT-3'
reacted with 1,3-indandione
Molecular weight: 2876.0
m/z^(ob): 2874.7

F | 5'-AGATC^(s)GTAT-3'
reacted with diethyl malonate
Molecular weight: 2847.9
m/z^(ob): 2845.4

Figure 1

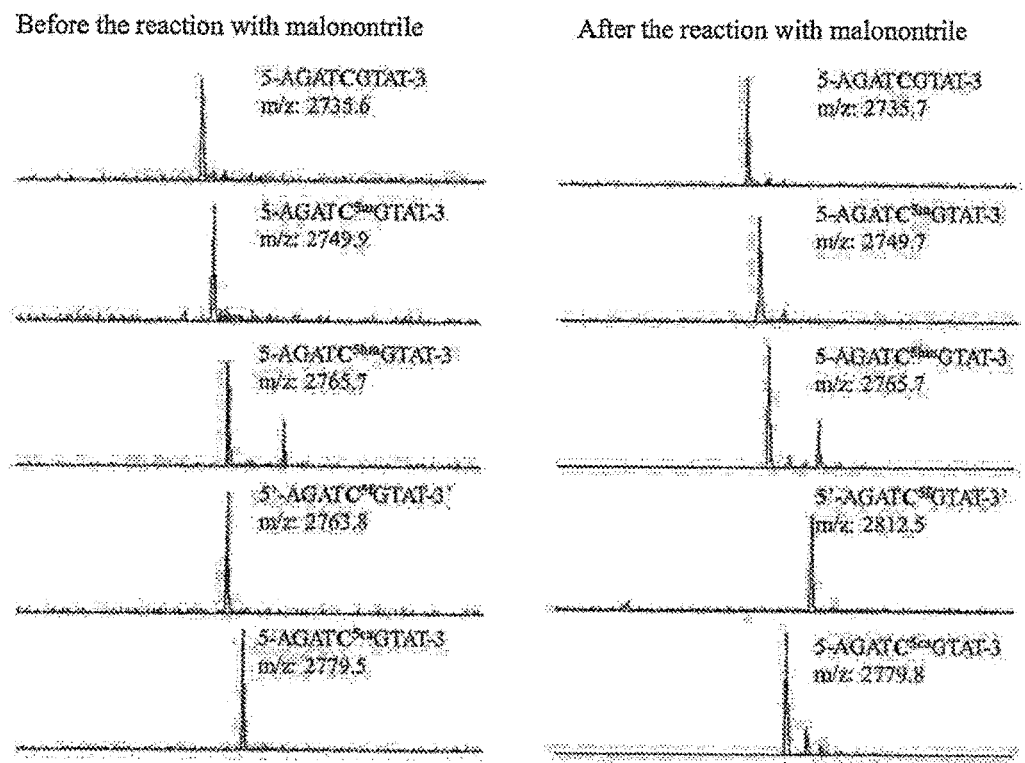
Figure 2
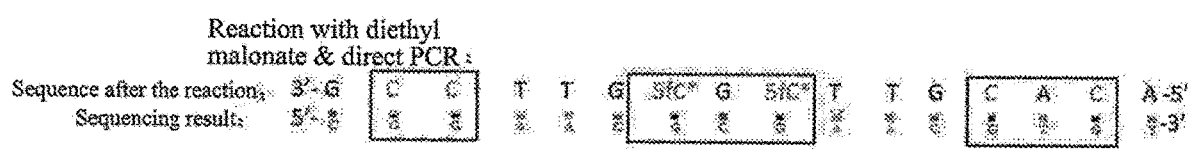
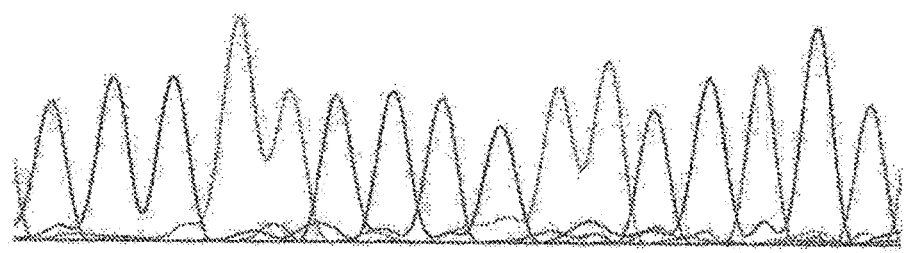
Figure 3A

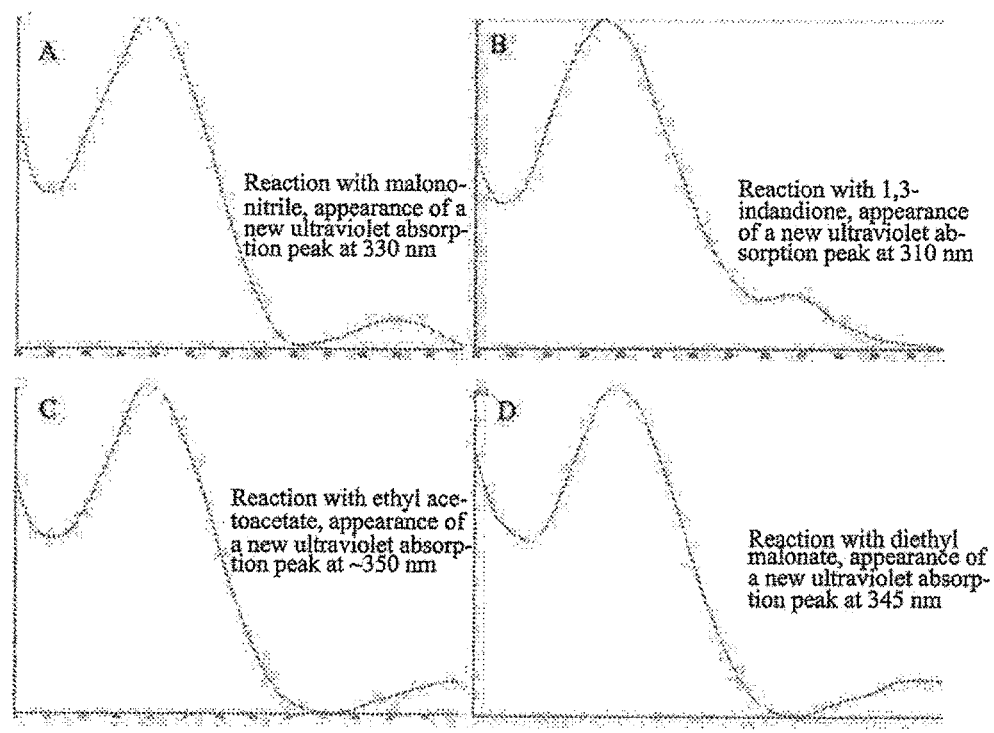
Figure 10
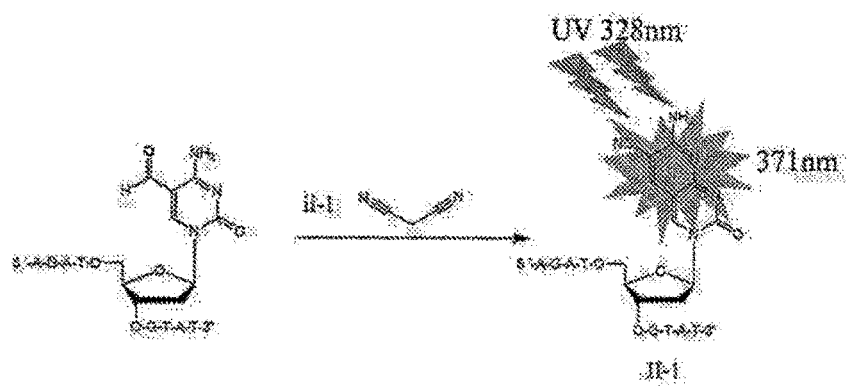
The fluorescence excitation spectrum and emission spectrum of the reaction product with malononitrile
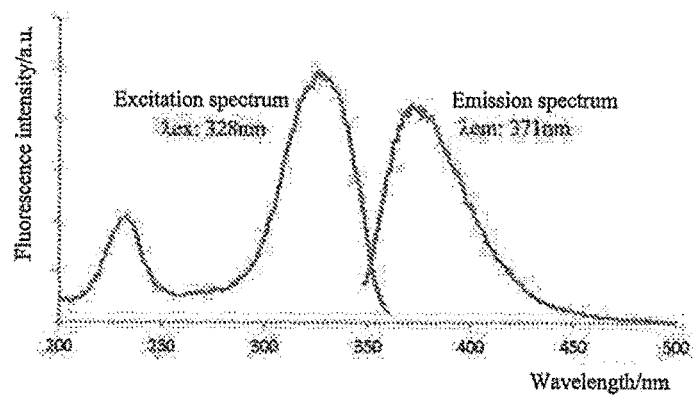
Figure 11

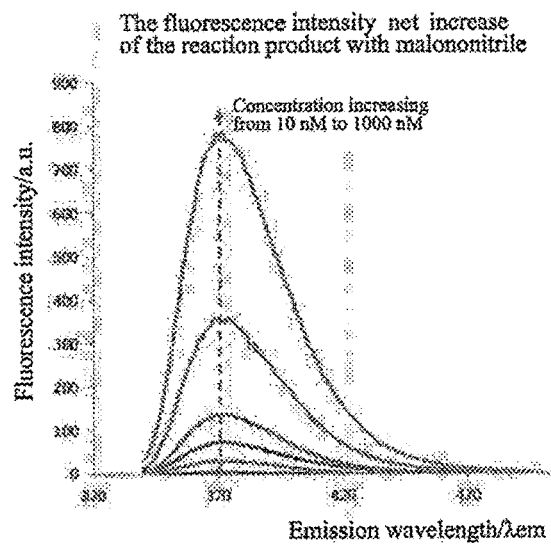 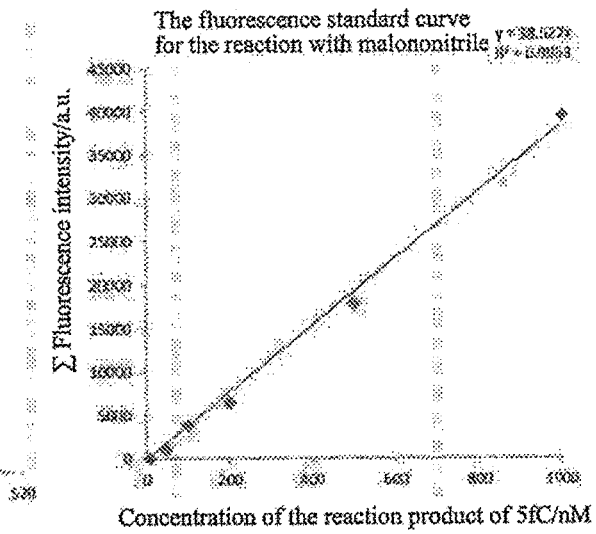
Figure 12A
Figure 12B
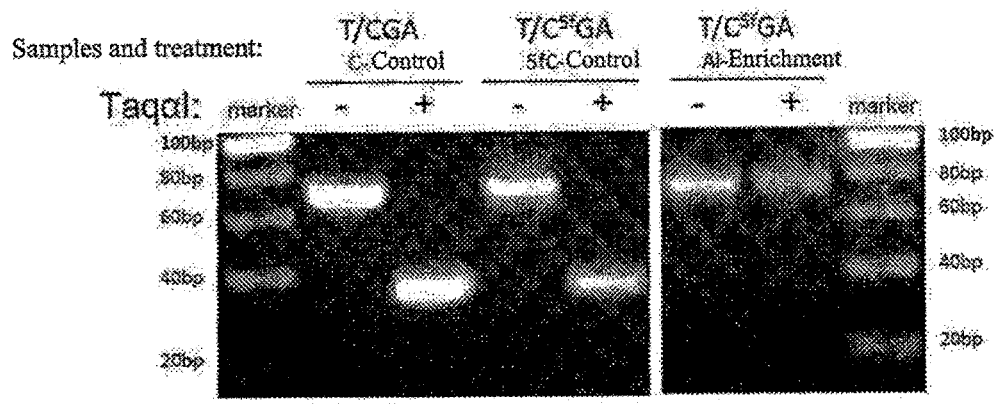
Figure 13

| Cytosine and related derivates thereof | Read results of conventional sequencing | Read results of sodium bisulfite sequencing | Read results of "5fC ring protecting sodium bisulfite sequencing technique" | Read results of "ring formation promoting 5fC to T transition sequencing technique" |
|---|---|---|---|---|
| C | C | T | T | C |
| 5mC | C | C | C | C |
| 5hmC | C | C | C | C |
| 5fC | C | T | C | T |
| 5caC | C | T | T | C |

Figure 16

SEQUENCE LISTING

<160> NUMBER OF SEQ ID NOS: 26

<210> SEQ ID NO 1
<211> LENGTH: 77
<212> TYPE: DNA
<213> ORGANISM: Artificial Sequence
<220> FEATURE:
<223> OTHER INFORMATION: Synthesized Oligonucleotide
<220> FEATURE:
<221> NAME/KEY: 5-formylcytosine (5fC)
<222> LOCATION: (41)..(41)
<220> FEATURE:
<221> NAME/KEY: 5-formylcytosine (5fC)
<222> LOCATION: (43)..(43)

<400> SEQUENCE: 1
cctcaccatc tcaaccaata ttatattatg tctacacgtt cgcgttccgt gttataatat     60
tgagggagaa gtggtga                                                   77

<210> SEQ ID NO 2
<211> LENGTH: 77
<212> TYPE: DNA
<213> ORGANISM: Artificial Sequence
<220> FEATURE:
<223> OTHER INFORMATION: Synthesized Oligonucleotide

<400> SEQUENCE: 2
tcaccacttc tccctcaata ttataacacg gaacgcgaac gtgtagacat aatataatat    60
tggttgagat ggtgagg                                                  77

<210> SEQ ID NO 3
<211> LENGTH: 30
<212> TYPE: DNA
<213> ORGANISM: Artificial Sequence
<220> FEATURE:
<223> OTHER INFORMATION: Synthesized Oligonucleotide

<400> SEQUENCE: 3 ccctttatt attttaatta atattatatt                                     30

<210> SEQ ID NO 4
<211> LENGTH: 80
<212> TYPE: DNA
<213> ORGANISM: Artificial Sequence
<220> FEATURE:
<223> OTHER INFORMATION: Synthesized Oligonucleotide

<400> SEQUENCE: 4
ctccgacatt atcactacca tcaaccaccc atcctacctg gactacattc ttattcagta    60
ttcaccactt ctccctcaat                                               80

<210> SEQ ID NO 5
<211> LENGTH: 20
<212> TYPE: DNA
<213> ORGANISM: Artificial Sequence
<220> FEATURE:
<223> OTHER INFORMATION: Synthesized Oligonucleotide

<400> SEQUENCE: 5
ctccgacatt atcactacca                                               20

<210> SEQ ID NO 6
<211> LENGTH: 145
<212> TYPE: DNA
<213> ORGANISM: Artificial Sequence
<220> FEATURE:
<223> OTHER INFORMATION: Synthesized Oligonucleotide
<220> FEATURE:
<221> NAME/KEY: 5-formylcytosine (5fC)
<222> LOCATION: (100)..(100)

<400> SEQUENCE: 6
catgagtgcc ctcagcagta agtaactgac cagatctctc gtgcctcttg aggctactga    60
gttatccaac ctttaggagc catgcatcga tagcatccgc cacaggcagt gaggctactg   120
agtcatgcac gcagaaagaa atagc                                        145

<210> SEQ ID NO 7
<211> LENGTH: 110
<212> TYPE: DNA
<213> ORGANISM: Artificial Sequence
<220> FEATURE:
<223> OTHER INFORMATION: Synthesized Oligonucleotide -continued

<400> SEQUENCE: 7
attcactccc actgagactg tggatcaggc caacatacat gccttcagta actgaccaga     60
tctcttagtt ctcttgaggc tactgagtta gaatggcaga gtcaaggagc              110

<210> SEQ ID NO 8
<211> LENGTH: 84
<212> TYPE: DNA
<213> ORGANISM: Artificial Sequence
<220> FEATURE:
<223> OTHER INFORMATION: Synthesized Oligonucleotide

<400> SEQUENCE: 8
ctacgcaaac tggctgtcaa agtaactgac cagatctctc ggctctcttg aggctactga     60
gttatcatgg acgctacctc acag                                           84

<210> SEQ ID NO 9
<211> LENGTH: 20
<212> TYPE: DNA
<213> ORGANISM: Artificial Sequence
<220> FEATURE:
<223> OTHER INFORMATION: Synthesized Oligonucleotide

<400> SEQUENCE: 9
catgagtgcc ctcagcagta                                                20

<210> SEQ ID NO 10
<211> LENGTH: 20
<212> TYPE: DNA
<213> ORGANISM: Artificial Sequence
<220> FEATURE:
<223> OTHER INFORMATION: Synthesized Oligonucleotide

<400> SEQUENCE: 10 tccaacctttt aggagccatg                                               20

<210> SEQ ID NO 11
<211> LENGTH: 20
<212> TYPE: DNA
<213> ORGANISM: Artificial Sequence
<220> FEATURE:
<223> OTHER INFORMATION: Synthesized Oligonucleotide

<400> SEQUENCE: 11
aggccaacat acatgccttc                                                20

<210> SEQ ID NO 12
<211> LENGTH: 20
<212> TYPE: DNA
<213> ORGANISM: Artificial Sequence
<220> FEATURE:
<223> OTHER INFORMATION: Synthesized Oligonucleotide

<400> SEQUENCE: 12
gaatggcaga gtcaaggagc                                                20

<210> SEQ ID NO 13
<211> LENGTH: 20
<212> TYPE: DNA
<213> ORGANISM: Artificial Sequence
<220> FEATURE:
<223> OTHER INFORMATION: Synthesized Oligonucleotide

<400> SEQUENCE: 13
ctacgcaaac tggctgtcaa                                                20

```
<210> SEQ ID NO 14
<211> LENGTH: 20
<212> TYPE: DNA
<213> ORGANISM: Artificial Sequence
<220> FEATURE:
<223> OTHER INFORMATION: Synthesized Oligonucleotide

<400> SEQUENCE: 14
ctgtgaggta gcgtccatga                                                   20

<210> SEQ ID NO 15
<211> LENGTH: 76
<212> TYPE: DNA
<213> ORGANISM: Artificial Sequence
<220> FEATURE:
<223> OTHER INFORMATION: Synthesized Oligonucleotide
<220> FEATURE:
<221> NAME/KEY: 5-formylcytosine (5fC)
<222> LOCATION: (38)..(38)
<220> FEATURE:
<221> NAME/KEY: 5-formylcytosine (5fC)
<222> LOCATION: (40)..(40)

<400> SEQUENCE: 15
cctcaccatc tcaaccaata ttatattacg cgtatatcgc gtatttcgcg ttataatatt       60
gagggagaag tggtga                                                       76

<210> SEQ ID NO 16
<211> LENGTH: 20
<212> TYPE: DNA
<213> ORGANISM: Artificial Sequence
<220> FEATURE:
<223> OTHER INFORMATION: Synthesized Oligonucleotide

<400> SEQUENCE: 16
cctcaccatc tcaaccaata                                                   20

<210> SEQ ID NO 17
<211> LENGTH: 76
<212> TYPE: DNA
<213> ORGANISM: Artificial Sequence
<220> FEATURE:
<223> OTHER INFORMATION: Synthesized Oligonucleotide
<220> FEATURE:
<221> NAME/KEY: 5-formylcytosine (5fC)
<222> LOCATION: (38)..(38)

<400> SEQUENCE: 17
cctcaccatc tcaaccaata ttatattacg cgtatatcgc gtatttcgcg ttataatatt       60
gagggagaag tggtga                                                       76

<210> SEQ ID NO 18
<211> LENGTH: 70
<212> TYPE: DNA
<213> ORGANISM: Artificial Sequence
<220> FEATURE:
<223> OTHER INFORMATION: Synthesized Oligonucleotide
<220> FEATURE:
<221> NAME/KEY: 5-formylcytosine (5fC)
<222> LOCATION: (35)..(35)

<400> SEQUENCE: 18
cctcaccatc tcaaccaata ttatattagt atttcgatta cgcgttatta tattgaggga       60
gaagtggtga                                                              70
```

```
<210> SEQ ID NO 19
<211> LENGTH: 70
<212> TYPE: DNA
<213> ORGANISM: Artificial Sequence
<220> FEATURE:
<223> OTHER INFORMATION: Synthesized Oligonucleotide

<400> SEQUENCE: 19
tcaccacttc tccctcaata taataacgcg taatcgaaat actaatataa tattggttga      60
gatggtgagg                                                              70

<210> SEQ ID NO 20
<211> LENGTH: 70
<212> TYPE: DNA
<213> ORGANISM: Artificial Sequence
<220> FEATURE:
<223> OTHER INFORMATION: Synthesized Oligonucleotide

<400> SEQUENCE: 20
cctcaccatc tcaaccaata ttatattagt atttcgatta cgcgttatta tattgaggga      60
gaagtggtga                                                              70

<210> SEQ ID NO 21
<211> LENGTH: 70
<212> TYPE: DNA
<213> ORGANISM: Artificial Sequence
<220> FEATURE:
<223> OTHER INFORMATION: Synthesized Oligonucleotide

<400> SEQUENCE: 21
tcaccacttc tccctcaata taataacgcg taatcgaaat actaatataa tattggttga      60
gatggtgagg                                                              70

<210> SEQ ID NO 22
<211> LENGTH: 9
<212> TYPE: DNA
<213> ORGANISM: Artificial Sequence
<220> FEATURE:
<223> OTHER INFORMATION: Synthesized Oligonucleotide
<220> FEATURE:
<221> NAME/KEY: 5-formylcytosine (5fC)
<222> LOCATION: (5)..(5)

<400> SEQUENCE: 22 agatcgtat                                                               9

<210> SEQ ID NO 23
<211> LENGTH: 9
<212> TYPE: DNA
<213> ORGANISM: Artificial Sequence
<220> FEATURE:
<223> OTHER INFORMATION: Synthesized Oligonucleotide

<400> SEQUENCE: 23 agatcgtat                                                               9

<210> SEQ ID NO 24
<211> LENGTH: 9
<212> TYPE: DNA
<213> ORGANISM: Artificial Sequence
<220> FEATURE:
<223> OTHER INFORMATION: Synthesized Oligonucleotide
<220> FEATURE:
<221> NAME/KEY: 5-methylcytosine (5mC)
<222> LOCATION: (5)..(5)
```

```
<400> SEQUENCE: 24 agatcgtat                                                              9

<210> SEQ ID NO 25
<211> LENGTH: 9
<212> TYPE: DNA
<213> ORGANISM: Artificial Sequence
<220> FEATURE:
<223> OTHER INFORMATION: Synthesized Oligonucleotide
<220> FEATURE:
<221> NAME/KEY: 5-hydroxymethylcytosine (5hmC)
<222> LOCATION: (5)..(5)

<400> SEQUENCE: 25 agatcgtat                                                              9

<210> SEQ ID NO 26
<211> LENGTH: 9
<212> TYPE: DNA
<213> ORGANISM: Artificial Sequence
<220> FEATURE:
<223> OTHER INFORMATION: Synthesized Oligonucleotide
<220> FEATURE:
<221> NAME/KEY: 5-carboxycytosine (5caC)
<222> LOCATION: (5)..(5)

<400> SEQUENCE: 26 agatcgtat                                                              9
```

5-FORMYLCYTOSINE SPECIFIC CHEMICAL LABELING METHOD AND RELATED APPLICATIONS

FIELD OF THE INVENTION

The present invention relates to a chemical labeling and detecting method of an epigenetically modified base, the chemical synthesis of related compounds, and related use of the reaction method and the compounds, and especially to a specific chemical labeling method of 5-formylcytosine or a 1-substituted derivative thereof and related use of the compounds related to the method in aspects such as labeling, detection, sequencing, imaging, diagnosis and treatment, and the like.

BACKGROUND ART

In the field of epigenetics, the study of DNA methylation and demethylation is one of the most important subjects. Hypermethylation in gene control region usually leads to silence of downstream genes, whereas demethylation process is usually accompanied by activation of the expression of downstream genes, thereby participating in corresponding biological process. In mammals, DNA demethylation process is achieved by TET (Ten-Eleven Translocation) family proteins-mediated oxidation of 5-methylcytosine (5mC), to gradually produce 5-hydroxymethylcytosine (5hmC), 5-formylcytosine (5fC) and 5-carboxylcytosine (5caC), and by base excision repair pathway (Mamta Tahiliani, et al., Science, 2009, 324:931-935; Skirmantas Kriaucionis and Nathaniel Heintz, Science, 2009, 324:929-930; Toni Pfaffeneder, et al., Angewandte Chemie International Edition, 2011, 123: 7146-7150; Shinsuke Ito, et al., Science, 2011, 333:1300-1303; Yufei He, et al., Science, 2011, 333:1303-1307.).

An important premise on studying the biological function of such epigenetic bases is to know its distribution region in genome and specific sequence information. Bisulfite sequencing method is a well-known method for DNA methylation analysis, and can identify the sequence information of 5mC at single-base resolution. Normal cytosine C is converted to uracil by sodium bisulfate treatment, and is read as T by Polymerase Chain Reaction (PCR) amplification and sequencing. However, 5mC is still read as C in the process of Polymerase Chain Reaction amplification and sequencing due to the presence of 5-methyl with electron-donating effect, which results in the process of sodium bisulfite treatment being difficult to occur.

5hmC, 5fC and 5caC, as modified bases capable of being stably present in genome, may also have particular biological functions. It is thus ascertained that the genomic distributions of these three cytosine derivatives are very important information for exploring their functions. However, the presence of 5hmC, 5fC and 5caC results in the bisulfite sequencing being more complicate. In normal bisulfite sequencing, 5hmC is read as C, and both 5fC and 5caC are read as T (Michael J. Booth, et al., Science, 2012, 336: 934-937.). Therefore, there is a need for developing a new sequencing technique at single base resolution to identify the positions of these new modified bases. With the development of detection techniques and sequencing methods for 5hmC (Chunxiao Song, et al., Cell, 2011, 153:678-691; Adam B. Robertson, et al., Nucleic Acids Research, 2011, 39:e55; William A. Pastor, et al., Nature, 2011, 473:394-397; Chunxiao Song, et al., Nature Methods, 2012, 9:75-77; Michael J. Booth, et al., Science, 2012, 336:934-937; Miao Yu, et al., Cell, 2012, 149:1368-1380.), the biological function of 5hmC is already known to some extent. Although corresponding detection methods for 5fC and 5caC were explored (Eun-Ang Raiber, et al., Genome Biology, 2012, 13:R69; Li Shen, et al., Cell, 2013, 153:692-706; Chunxiao Song, et al., Cell, 2013, 153:678-691; Michael J. Booth, et al., Nature Chemistry, 2014, 6:435-440.), it is still immature in detecting the sequence distribution with low cost while achieving high-throughput and single-base resolution. Therefore, the studies on 5fC and 5caC are relatively retarded.

Currently, the studies on 5-formylcytosine related chemical reactions mainly focus on 5-formyl group on the cytosine ring. The researchers designed a reaction with respect to the formyl group of 5fC on the basis that formyl group can react with the amino of hydroxylamine compound and generate oxime (Shinsuke Ito, et al., Science, 2011, 333:1300-1303; Eun-Ang Raiber, et al., Genome Biology, 2012, 13:R69; Chunxiao Song, et al., Cell, 2013, 153:678-691.), and this reaction is used to detect the position of 5fC in genome. The method for labeling 5fC with fluorescence group is developed using the reaction between formyl and amino (Jianlin Hu, et al., Chemistry-A European Journal, 2013, 19:2013-5840.). The formyl group is reduced to hydroxymethyl with NaBH$_4$, so that 5fC is reduced to 5hmC, and the 5fC site is read as C in bisulfite sequencing process. Therefore, the position of 5fC base can also be identified in certain region (Chunxiao Song, et al., Cell, 2013, 153:678-691; Michael J. Booth, et al., Nature Chemistry, 2014, 6:2014-440.). These methods are early detection methods of 5fC, and promote the study of 5fC base. However, these methods suffer from many defects such as high background noise, high cost, complex operation, difficulty in sequencing at single-base resolution, and the like. Therefore, there is a need for developing a novel 5fC labeling and detecting method with high selectivity and high efficiency, which has a positive effect on further promoting the study of epigenetic demethylation.

SUMMARY OF THE INVENTION

An object of the invention is, in order to overcome the deficiencies present in prior art, to provide a specific chemical labeling method of 5-formylcytosine or a 1-substituted derivative thereof, which comprises the following steps:

reacting an active methylene compound containing a side-chain active group with 5-formylcytosine or a 1-substituted derivative thereof, wherein a dehydration condensation reaction occurs between an active methylene compound containing a side-chain active group and a 5-formyl group of cytosine in 5-formylcytosine or a 1-substituted derivative thereof, and at the same time an intramolecular reaction occurs between the side-chain active group of the active methylene compound and a 4-amino group of cytosine in the 5-formylcytosine or a 1-substituted derivative thereof to implement ring closing.

In order to clearly describe the content related to the invention, the structure formulas of 5-formylcytosine, 1-hydrogen substituted derivative of 5-formylcytosine, 5-formylcytosine deoxyribonucleoside and 5-formylcytosine ribonucleoside are shown as follows.

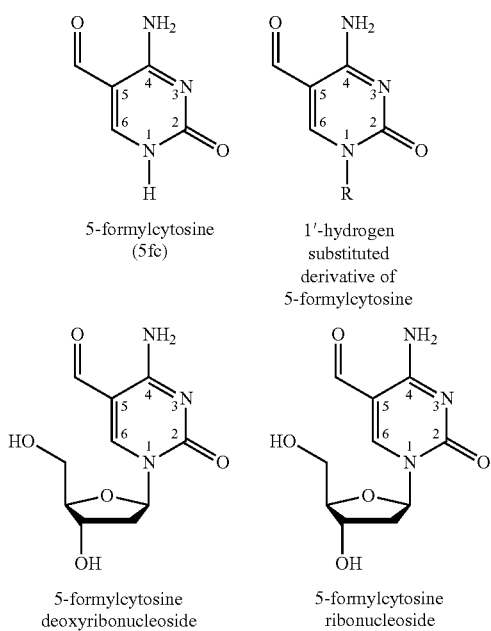

5-formylcytosine (5fc)

1'-hydrogen substituted derivative of 5-formylcytosine 5-formylcytosine deoxyribonucleoside 5-formylcytosine ribonucleoside For the convenience of describing, the term of "5-formylcytosine" or "5fC" below refers to 5-formylcytosine or all related 1-substituted derivatives thereof, unless otherwise specified. In this case, 1-substituted derivative of 5-formylcytosine can be selected from small molecular compounds or polymeric macromolecular compounds formed by binding the glucosidic bond in nucleoside or deoxynucleoside, nucleotide or deoxynucleotide, ribonucleic acid (RNA, single stranded or double stranded) or deoxyribonucleic acid (DNA, single stranded or double stranded) to 1-position of 5-formylcytosine (corresponding substituent R represents structures excluding 5-formylcytosine part in the molecule), which respectively results in 5-formylcytosine ribonucleoside or 5-formylcytosine deoxyribonucleoside, 5-formylcytosine ribonucleotide or 5-formylcytosine deoxyribonucleotide, 5-formylcytosine base-containing RNA or 5-formylcytosine base-containing DNA. In addition to the above ribosyl- or deoxyribosyl-containing derivatives, the substituent R of 1-substituted derivatives of 5-formylcytosine can also represent hydrocarbyl, or hydrocarbyl with a functional substituent such as —OH, —NH$_2$, —CHO and/or —COOH, and the like. The hydrocarbyl can be alkyl, cycloalkyl, alkenyl, or alkynyl, preferably C1-C30 linear or branched alkyl, C1-C30 linear or branched alkenyl, or C1-C30 linear or branched alkynyl, more preferably C1-C10 linear or branched alkyl, C1-C10 linear or branched alkenyl or C1-C10 linear or branched alkynyl. The substituent R, for example, includes but is not limited to —CH$_3$, —CH$_2$CH$_3$, —CHO, —CH$_2$CHO,

and the like.

The following is a general chemical reaction equation for the method of the present invention.

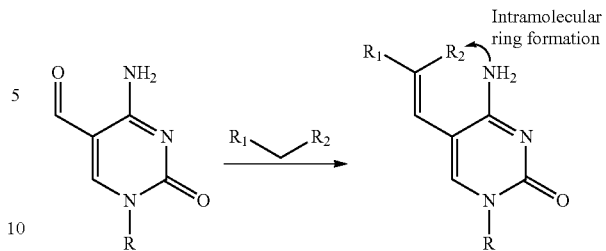

In the general reaction equation above:

One of the reaction raw materials is the above 5-formylcytosine or a 1-substituted derivative of 5-formylcytosine, which can be selected from related small molecular compounds or polymeric macromolecular compounds formed by binding the glucosidic bond in nucleoside or deoxynucleoside, nucleotide or deoxynucleotide, ribonucleic acid (RNA, single stranded or double stranded) or deoxyribonucleic acid (DNA, single stranded or double stranded) to 1-position of 5-formylcytosine (in which the corresponding substituent R represents the structure excluding 5-formylcytosine in the molecule), which respectively results in 5-formylcytosine ribonucleoside or 5-formylcytosine deoxyribonucleoside, 5-formylcytosine ribonucleotide or 5-formylcytosine deoxyribonucleotide, 5-formylcytosine base-containing RNA or 5-formylcytosine base-containing DNA. Moreover, the substituent R of 1-substituted derivatives of 5-formylcytosine can also represent hydrocarbyl, or hydrocarbyl with a functional substituent such as —OH, —NH$_2$, —CHO and/or —COOH, and the like. The hydrocarbyl can be alkyl, cycloalkyl, alkenyl, or alkynyl, preferably C1-C30 linear or branched alkyl, C1-C30 linear or branched alkenyl or C1-C30 linear or branched alkynyl, more preferably C1-C10 linear or branched alkyl, C1-C10 linear or branched alkenyl or C1-C10 linear or branched alkynyl. The substituent R, for example, includes but is not limited to —CH$_3$, —CH$_2$CH$_3$, —CHO, —CH$_2$CHO,

and the like.

The substituent R in the product is not influenced, and the options thereof are the same as those in the raw material.

In the active methylene compound containing a side-chain active group, R$_1$ can be selected from any electrondrawing group, preferably including but not limited to cyano, nitro, formyl, carbonyl compound

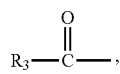

carboxylic acid and derivatives thereof such as

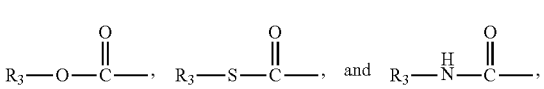

and the like; and most preferably, R$_1$ is cyano, formyl, carbonyl compound

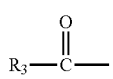

and ester compound

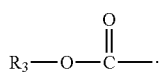

$R_2$ can be selected from any electrondrawing group, preferably including but not limited to cyano, formyl, carbonyl compound

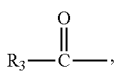

carboxylic acid and derivatives thereof such as

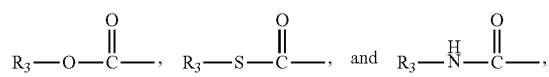

and the like; and most preferably $R_2$ is cyano, formyl, carbonyl compound

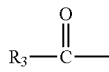

and ester compound

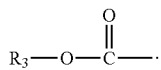

$R_3$ above represents hydrocarbyl, or hydrocarbyl with a functional substituent such as —OH, —NH$_2$, —CHO, —COOH and/or azido, biotin and the like, wherein the hydrocarbyl preferably is, but not limited to, C1-C30 linear or branched alkyl, alkenyl or alkynyl, and most preferably C1-C30 linear alkyl.

Above side chain groups $R_1$ and $R_2$ can form a ring directly by bonding with each other, or form a ring indirectly by bonding via an atom such as C, N, O, and the like.

The design of the labeling method and the related compounds of the present invention takes both the 5-formyl group and the 4-amino group of 5fC base cytosine ring into consideration, and a new 5fC labeling method is developed with considering both of them together. A ring closing is achieved by the condensation reaction between the active methylene and the formyl group, and then the intramolecular reaction between the active side-chain group $R_2$ (such as formyl, carbonyl, cyano, ester bond, and the like) of the active methylene compound and 4-amino group. Based on this concept, the labeling method of the present invention in which 5-formylcytosine is selectively reacted is developed, and a series of related methods and the applications of the compounds are developed, which provides various effective study means to the study of nucleic acid chemistry and the study of epigenetics.

In an aspect of the present invention, the active methylene compound containing a side-chain active group is compound i as shown in the general formula below. The compound i reacts with 5-formylcytosine or a 1-substituted derivative thereof in one step to synthesize compound I as shown in the general formula below:

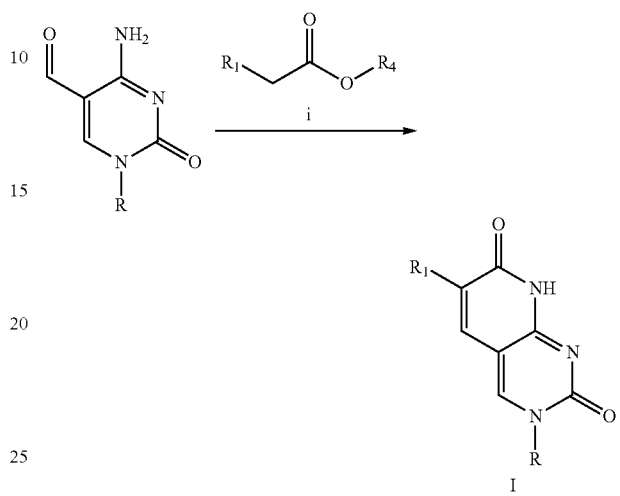

In the chemical equation above:

One of the reaction raw materials is 5-formylcytosine or a 1-substituted derivative of 5-formylcytosine, and the options for the substituted derivative and substituent R are the same as those shown in aforementioned general formula; and the substituent R in the product is not influenced, and the options thereof are the same as those in the reaction raw material.

The active side-chain group $R_1$ of compound i can be selected from any electrondrawing group as previously described.

$R_4$ represents hydrocarbyl, or hydrocarbyl with a functional substituent such as —OH, —NH$_2$, —CHO and/or —COOH, and the like, wherein the hydrocarbyl preferably is but not limited to C1-C30 linear or branched alkyl, alkenyl or alkynyl, and most preferably is C1-C10 linear or branched alkyl.

In some embodiments, the reaction condition for synthesizing compound of formula I with compound i and 5-formylcytosine as raw materials can be in an alkaline organic solution, preferably a solution of potassium carbonate or sodium hydroxide in methanol; at a reaction temperature of room temperature to 50° C., preferably 37° C.; and for a reaction time of 12-48 hours, preferably 24 hours. The reaction yield is greater than or equal to 95%. In the reaction, the active methylene between $R_1$ and carbonyl group nucleophilically attacks the carbon atom of the 5-formyl of 5fC base in an alkaline condition, and an olefinic bond is formed by dehydration condensation; and then an intramolecular reaction occurs, in which the 4-amino group in the cytosine ring attacks the ester bond in compound i, and then an amide is formed by removing the alcohol compound having R4 as side chain and forming a ring.

In an embodiment, $R_1$ is acetyl, and $R_4$ is methyl or ethyl, which means compound i is methyl acetoacetate or ethyl acetoacetate. In another embodiment, $R_1$ is ethoxyl carbonyl, and $R_4$ is ethyl, which means compound i is diethyl malonate. In yet another embodiment, $R_1$ is 4-azido butanoyl, and $R_4$ is ethyl, which means compound i is ethyl 6-azido-3-oxyhexanoate.

All the compounds in the above embodiments are proved to be useful in "5fC ring-protecting sodium bisulfite sequencing technique", and be able to identify the position of 5fC base in a nucleotide sequence at single-base resolution.

In a second aspect of the present invention, the above active methylene compound containing a side-chain active group is compound ii as shown in the general formula ii below. The compound ii reacts with 5-formylcytosine or a 1-substituted derivative thereof in one step to synthesize compound II as shown in the general formula below:

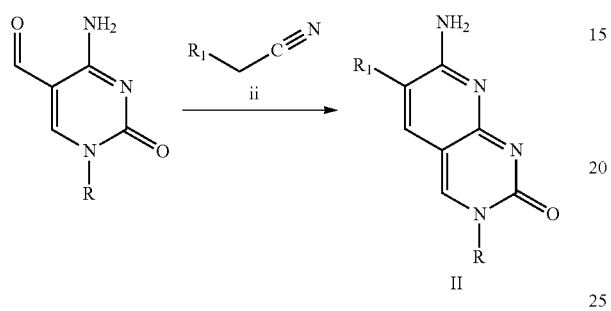

In the chemical equation above:

One of the reaction raw materials is 5-formylcytosine or a 1-substituted derivative of 5-formylcytosine, and the options for the substituted derivative and substituent R are the same as those shown in aforementioned general formula; and the substituent R in the product is not influenced, and the options thereof are the same as those in the reaction raw material.

$R_1$ can be selected from any electrondrawing group, and the options thereof are the same as those set forth.

In some embodiments, the reaction condition for synthesizing compound of formula II with compound ii and 5-formylcytosine as raw materials can be in an acidic to neutral aqueous solution, preferably a weak acidic aqueous solution, most preferably a weak acidic aqueous solution of pH 5-7; at a reaction temperature of room temperature to 50° C., preferably 37° C.; and for a reaction time of 12-48 hours, preferably 24 hours. The reaction yield can reach greater than or equal to 98%. In the reaction, the active methylene between $R_1$ and cyano group attacks the 5-formyl of 5fC base, and an olefinic bond is formed by dehydration condensation; and then an intramolecular reaction occurs, in which the amino group in the cytosine ring attacks the carbon atom of the cyano group in compound ii, and a ring is formed through addition reaction.

In an embodiment, $R_1$ is also a cyano group, which means compound ii is malononitrile.

In this particular embodiment, the reaction product of malononitrile and 5fC is read as thymine T in PCR, and can be used in "ring formation promoting 5fC to T conversion sequencing technique" to directly detect the position of 5fC base in genome.

In a third aspect of the invention, the above active methylene compound containing a side-chain active group is compound iii as shown in the general formula iii below. The compound iii reacts with 5-formylcytosine or a 1-substituted derivative thereof in one step to synthesize compound III as shown in the general formula III below:

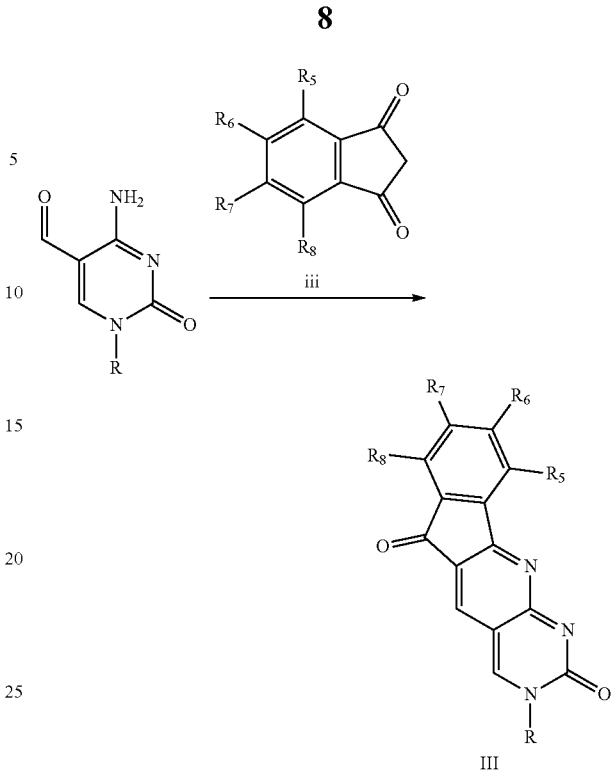

In the chemical equation above:

One of the reaction raw materials is 5-formylcytosine or a 1-substituted derivative of 5-formylcytosine, and the options for the substituted derivative and substituent R are the same as those shown in aforementioned general formula; and the substituent R in the product is not influenced, and the options thereof are the same as those in the reaction raw material.

$R_5$, $R_6$, $R_7$ and $R_8$ each independently can be selected from hydrogen atom H or hydrocarbyl, or hydrocarbyl with a functional substituent such as —OH, —O—, —NH$_2$, —NH—, —CHO, —COOH and/or azido, biotin and the like. $R_5$, $R_6$, $R_7$ and $R_8$ each independently can also be selected from —OH, —NH$_2$, —CHO, —COOH, —CN, —NO$_2$ azido and the like, wherein the hydrocarbyl preferably is C1-C30 linear or branched alkyl, alkenyl or alkynyl, and most preferably is C1-C10 linear alkyl.

In some embodiments, the reaction condition for synthesizing compound III with compound iii and 5-formylcytosine as raw materials can be in an alkaline organic solution, preferably a solution of potassium carbonate or sodium hydroxide in methanol; at a reaction temperature of room temperature to 50° C., preferably 37° C.; and for a reaction time of 12-48 hours, preferably 24 hours. The reaction condition can also be in an acidic to neutral aqueous solution, preferably a weak acidic aqueous solution, most preferably a weak acidic aqueous solution of pH 5-7; at a reaction temperature of room temperature to 50° C., preferably 37° C.; and for a reaction time of 12-48 hours, preferably 24 hours. The reaction yield can reach greater than or equal to 95%. In the reaction, the active methylene between the two dicarbonyl groups in the five-membered ring of compound iii is dehydrated and condensed with the 5-formyl of 5fC base; and then an intramolecular reaction occurs, in which the amino group in the cytosine ring attacks the carbonyl group in compound iii, and a conjugated tetracyclic compound III is formed by dehydration condensation and ring formation.

In an embodiment, compound iii is 1,3-indandione.

In preferred examples, the above raw material compound iii can be a derivative iv of compound iii as shown in the general formula iv.

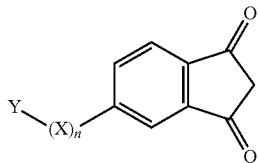

In formula iv:

X constitutes a linker sequence to introduce a functional group Y, wherein:

X is the basic unit for constituting the linker sequence, and X can be C1-05 linear or branched hydrocarbyl, or C1-05 linear or branched hydrocarbyl with ether bond —O— and/or imino group —NH—; preferably X is —CH$_2$—, —O—CH$_2$—CH$_2$—, —CH$_2$—O—CH$_2$— or —CH$_2$—CH$_2$—O—. The constituted linker sequence (X)$_n$ can be a combination of kinds of above basic structure unit X in any portion and any order;

n can be a positive integer greater than or equal to 1;

Y is a special functional group, which can be selected from biotin, azido, alkynyl or alkynyl derivative, wherein the alkynyl is preferably C2-C20 alkynyl, and the alkynyl derivative is preferably any alkynyl derivative ranging from C2-C20; and Y is more preferably biotin, azido, ethynyl or cyclooctynyl.

In some embodiments, X can be —CH$_2$—, n can be a positive integer between 1 and 9, and Y can be azido.

In an embodiment, compound iv is 5-(2-azidoethyl)-1,3-indandione, also called Azido Indanedione (AI) for short, X is methylene —CH$_2$—, with two units connected in series (i.e., n=2), and Y is azido.

The reaction product of the compound of above formula iii or formula iv and 5fC base can be read as thymine T in PCR, and can be used to directly detect the position of 5fC base in genome.

Another object of the present invention is to provide the following novel compounds related to the 5-formylcytosine specific labeling method mentioned above:

I. A compound, the general formula of which is as shown in formula I:

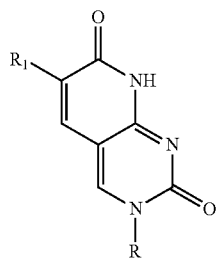

In formula I, the structure excluding R is called base analog. If R is bonded to 1-position of this base analog, it can be ribosyl or deoxyribosyl, or 5'- or 3'-phosphate-modified ribosyl or deoxyribosyl, and can also be the structure excluding the base analog of formula I of small molecular compound or polymeric macromolecular compound formed by binding glucosidic bond in ribonucleic acid (RNA, single stranded or double stranded) or deoxyribonucleic acid (DNA, single stranded or double stranded) to 1-position of the base analog of formula I. R can also represent hydrogen, hydrocarbyl, or hydrocarbyl with a functional substituent such as —OH, —NH$_2$, —CHO and/or OH and the like; preferably, R is but not limited to C1-C30 linear or branched alkyl, alkenyl or alkynyl, or C1-C30 linear or branched alkyl, alkenyl or alkynyl with a functional group such as —OH, —NH$_2$, —CHO and/or —COOH and the like; and most preferably, R is —CH$_3$, —CH$_2$CH$_3$, —CHO, —CH$_2$CHO,

and the like.

R$_1$ can be selected from any electrondrawing group, and preferably is but not limited to cyano, formyl, carbonyl compound

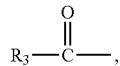

carboxylic acid and a derivative thereof such as

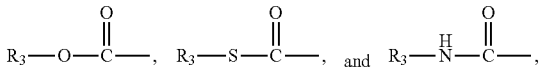

and the like; and most preferably, R$_1$ is cyano, formyl, carbonyl compound

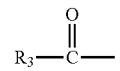

and ester compound

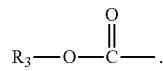

R$_3$ above represents hydrocarbyl, or hydrocarbyl with a functional substituent such as —OH, —NH$_2$, —CHO, —COOH and/or azido and the like, wherein the hydrocarbyl preferably is but not limited to C1-C30 linear or branched alkyl, alkenyl or alkynyl, and most preferably is C1-C30 linear alkyl.

II. A compound, the general formula of which is as shown in formula II:

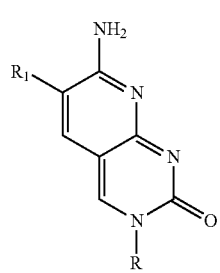

In formula II, the options for R is same as those for R in formula I, and the options for $R_1$ is same as those for $R_1$ in formula I.

III. A compound, the general formula of which is as shown in formula III:

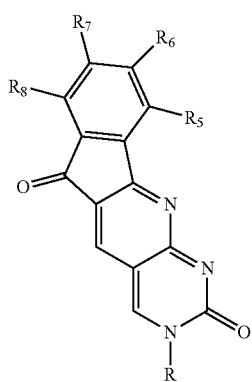

III

In formula III, the options for R is same as those for R in formula I. $R_5$, $R_6$, $R_7$ and $R_8$ each can independently be selected from hydrogen H or hydrocarbyl, or hydrocarbyl with a functional substituent such as —OH, —O—, —$NH_2$, —NH—, —CHO, —COOH and/or azido, biotin and the like. $R_5$, $R_6$, $R_7$ and $R_3$ each can also independently be selected from —OH, —$NH_2$, —CHO, —COOH, —CN, —$NO_2$ azido and the like, wherein the hydrocarbyl preferably is C1-C30 linear or branched alkyl, alkenyl or alkynyl, and most preferably is C1-C10 linear alkyl.

The novel compounds above can be obtained directly by the specific chemical labeling method of 5-formylcytosine or a 1-substituted derivative thereof as set forth, and can also be obtained by other organic synthesis methods.

Yet another object of the invention is to provide various applications employing the specific chemical labeling method of 5-formylcytosine or a 1-substituted derivative thereof of the present invention in the aspect such as labeling, sequencing, detection, imaging, and diagnosis. The particular applications are as below.

In the present invention, the method for specific chemical labeling 5-formylcytosine or a 1-substituted derivative thereof with an active methylene compound containing a side-chain active group or the above active methylene compound containing a side-chain active group are used in the applications of (1) sequencing analysis of sequence distribution information of 5-formylcytosine and/or single-base resolution sequence information in genome;

(2) detection of the sequence position of 5-formylcytosine in a nucleic acid molecule by single-base resolution sequencing;

(3) detection of the content of 5-formylcytosine or a 1-substituted derivative thereof;

(4) directly or indirectly enrichment of DNA or RNA molecule containing 5-formylcytosine base;

(5) design for preparing a kit for detecting distribution information of 5-formylcytosine and/or single-base resolution sequence information in genomic DNA sample;

(6) influence on the identification and binding ability, or enzyme activity of a nucleic acid binding protein, wherein the nucleic acid binding protein comprises a nucleic acid polymerase and/or restriction endonuclease; and (7) related aspects of molecular diagnosis involving 5-formylcytosine.

The above active methylene compound containing a side-chain active group mainly refers to aforementioned four kinds of compounds of i, ii, iii, and iv (i.e., the above compounds i, ii, iii, and iv).

The above genomic DNA sample or RNA sample can be derived from cell culture, animal tissue, animal blood, formalin-fixed tissue, paraffin-embedded tissue, and trace sample such as early development sample of embryo, single cell and the like.

Yet another object of the invention is to provide various applications of 5-formylcytosine-related conjugated polycyclic compound in the aspect such as labeling, sequencing, detection, imaging, diagnosis and the like. The particular applications are as the following applications in:

(1) nucleic acid sequencing;

(2) sequencing detection of distribution information of 5-formylcytosine and/or single-base resolution sequence information in a nucleic acid molecule;

(3) fluorescence spectrometric analysis of the content of 5-formylcytosine;

(4) in vivo or in vitro imaging technique of 5-formylcytosine;

(5) specific labeling of a nucleic acid sequence;

(6) detection of the content of 5-formylcytosine or a 1-substituted derivative thereof;

(7) directly or indirectly enrichment of a molecule containing 5-formylcytosine base;

(8) aspects such as study of nucleic acid-protein interaction and nucleic acid-nucleic acid interaction and the like; and (9) nucleic acid modification-related molecular diagnosis.

The above 5-formylcytosine-related conjugated polycyclic compound refers to aforementioned three kinds of compounds I, II and III.

The above applications of 5-formylcytosine-related conjugated polycyclic compounds comprise the applications which directly use the currently available conjugated polycyclic compounds, and also comprise the applications which use the products indirectly obtained from the reaction of 5-formylcytosine and/or a 1-substituted derivative thereof with compound i, ii, iii or iv.

Yet another object of the invention is to provide various kits for detecting 5-formylcytosine base, which comprise the aforementioned active methylene compound containing a side-chain active group (for example, compound i, ii, iii, or iv) and corresponding reaction solvent.

In an embodiment, the kits above can be used to achieve single-base resolution analysis of distribution information of 5-formylcytosine and/or single-base resolution sequence information in genome.

Yet another object of the invention is to provide a method for detection and sequencing analysis of other modified cytosine bases including 5-methylcytosine (5mC), 5-hydroxymethylcytosine (5hmC), and 5-carboxylcytosine (5caC). The methods for detection and sequencing analysis of other modified cytosine bases are all based on various methods for 5-formylcytosine above. Based on disclosed conversion methods, the conversion of other modified cytosine to 5-formylcytosine can be achieved, and thus the detection and sequencing analysis of targeting modified cytosine can be implemented with corresponding method for 5-formylcytosine. For example, 5mC can be oxidized by a specifically screened oxidase CcTET1 to stay in 5fC phase (Liang Zhang, et al, Journal of American Chemical Society, 2014, 136:4801-4804.); 5hmC can be specifically oxidized by an inorganic compound of potassium perruthenate KRuO4 to 5fC (Michael J. Booth, et al., Science, 2012, 336:934-937.); and theoretically the detection and sequencing analysis of 5-formylcytosine can also be implemented by reducing 5-carboxylcytosine to 5-formylcytosine.

The design of the labeling method and the related compound of the present invention take both the 5-formyl group and the ortho-4-amino group of 5fC base cytosine ring into consideration. A new 5fc labeling method is developed with considering both of them together and thereby improves the selectivity of reaction. A series of related methods and the applications of the compounds are developed, which provide various effective study means to the study of nucleic acid chemistry and the study of epigenetics.

Further, with the reaction of a specifically screened active methylene compound and 5-formylcytosine or a 1-substituted derivative thereof, in combination with techniques such as, sequencing technique of nucleic acid (DNA or RNA) sequence, fluorescence spectrometric analysis, or the like, the present invention can establish a method for specifically labeling and specifically enriching 5-formylcytosine or a 1-substituted derivative thereof, and a sequencing method of single-base resolution analysis of 5-formylcytosine at the whole genome scale. In combination of disclosed methods, the invention can also be used for the detection and sequencing analysis of other modified cytosines, such as 5-methylcytosine, 5-hydroxymethylcytosine, and 5-carboxylcytosine. Moreover, the compounds of the present invention also have promising values in the aspects such as fluorescence labeling, sequencing, intracellular imaging detection and the like.

The method of the present invention overcomes existed deficiencies in prior art, such as high background noise, difficulty in realizing single-base resolution sequencing, high cost and the like, and can achieve labeling 5-formylcytosine or a 1-substituted derivative thereof with high-selectivity, high specificity, high efficiency and low cost.

The kits for detecting 5-formylcytosine base provided by the present invention can easily and quickly perform whole-genome analysis of distribution information of 5-formylcytosine, achieve single-base resolution sequencing analysis of the whole genomic sequence information of 5-formylcytosine, and make it possible to commercially detect 5fC base with low cost.

Moreover, the present invention provides compounds I, II, and III, which are conjugate polycyclic (the number of rings ≥2) compounds derived from 5fC cytosine. These compounds have good fluorescence property, and therefore can be used for studies related to nucleic acid.

BRIEF DESCRIPTION OF THE DRAWINGS

FIG. 1 is the mass spectrometry results of 9-base DNA, i.e., 5'-AGA TC$^{5f}$G TAT-3' and those obtained after the reaction of such 9-base DNA with 5 representatives of compounds i, ii and iii in example 1.

FIG. 2 is the mass spectrometry results of 5 kinds of 9-base DNA sequences before and after the reaction with malononitrile in example 1, wherein each 9-base DNA sequence has one kind of cytosine different from that in the other 9-base DNA sequences. The results show the selectivity of the reaction in the present invention.

FIGS. 3A and 3B show that "5fC ring formation protecting sodium bisulfite sequencing technique" is implemented with compound i of diethyl malonate in example 2, wherein 5fC* represents the product obtained after the reaction of 5fC.

FIG. 10 shows new ultraviolet absorption peaks produced from the reaction of 9-base DNA, i.e. 5-AGA TC$^{5f}$G TAT-3, respectively with 4 kinds of compounds of malononitrile (A), 1,3-indandione (B), ethyl acetoacetate (C) and diethyl malonate (D), shown by Thermo Nanodrop Micro-Ultraviolet Spectrophotometer in example 6.

FIG. 11 shows the fluorescent activation effect produced by the reaction of 5fC bases with malononitrile in example 6.

FIG. 12A shows the net increase of fluorescence intensity at different concentrations of the reaction product of Oligo NO.1 and malononitrile in example 6. In the diagram, the concentrations represented by curves from bottom to top are respectively 10 nM, 50 nM, 100 nM, 200 nM, 500 nM and 1000 nM in order. FIG. 12B is a linear relation diagram of the net increase of fluorescence intensity of the reaction product versus the concentration thereof.

FIG. 13 shows the double-stranded DNA sequence after the reaction with TaqαI indigestible compound AI in example 7.

FIG. 16 shows the comparison between the sequencing read results from "5fC ring formation protecting sodium bisulfite sequencing", "ring formation promoting 5fC to T conversion sequencing technique", conventional sequencing, and sodium bisulfite sequencing.

DETAILED DESCRIPTION OF THE INVENTION

Figure 3B:
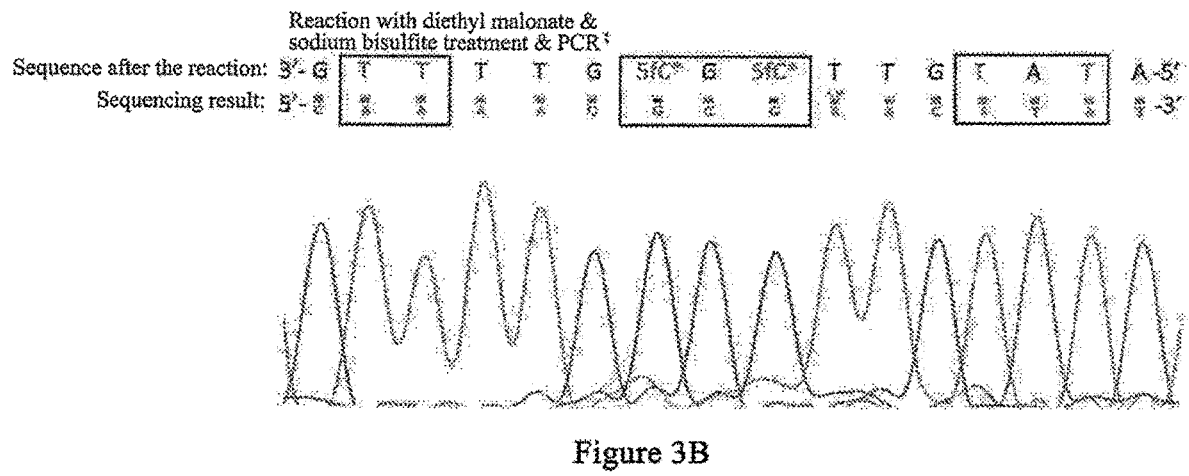

The novel compounds, the synthesis methods and reaction conditions, the related applications of the compounds and methods of the present invention will be described in detail below, in order to clearly describe the contents of the present invention.

The invention relates to the application of the 5-formylcytosine-related conjugate polycyclic compound.

Any conjugate polycyclic compound having a structure of the aforementioned 3 kinds of structures of compounds I, II, or III applies to the present invention. The synthesis methods of the new structure compounds of compounds I, II, and III are not limited to the synthesis methods of the present invention. No matter whether the synthesis methods thereof have difference, they apply to 3 kinds of compounds of the present invention.

3 kinds of compounds provided by the invention can be used in studies on nucleic acids. 3 kinds of compounds of the invention generate fluorescence under certain excitation light conditions, and thus can be used as a new category of fluorescent bases to apply in research areas such as study on kinetics problem of nucleic acid base conformation, interaction between other molecules (such as protein) with nucleic acid, nucleic acid-nucleic acid interaction, the chemical environments where a nucleic acid is present, and the like. Meanwhile, 3 kinds of fluorescent bases provided by the invention can be introduced from 5fC bases. In use, the corresponding phosphoramidite monomer of 5fC base can firstly be used to replace target fluorescent base to synthesize DNA, and then the fluorescent bases are introduced by the reaction of the present invention when necessary. Therefore, the feasibility of applying these 3 kinds of fluorescent bases is higher than that of other commercially available non-natural fluorescent bases.

Related Applications of 5-formylcytosine Specific Chemical Labeling Method of the Present Invention 1. Specific Chemical Labeling of 5fC (1) Direct Labeling of 5fC 5-formylcytosine is directly labeled with this method. Particularly, 5-formylcytosine can be reacted with the compounds of the present invention under the reaction condition of the present invention, such that it is converted into a new cytosine conjugate polycyclic derivative compound, thereby incorporating new chemical properties, for example, new ultraviolet absorption spectrum and fluorescence emission spectrum. The new chemical properties of the obtained product can be used to indicate 5-formylcytosine, achieving labeling of 5-formylcytosine, and a new labeling method is provided for studying dynamic change of intracellular epigenetics. Quantitative analysis of 5-formylcytosine base in unknown nucleic acid samples can also be performed by making use of the special absorption spectrum or fluorescence emission spectrum of the reaction products I, II or III.

In an embodiment of the invention, by means of the reaction of malononitrile with oligomeric deoxyribonucleotide chain containing 5fC base, a working curve of concentration versus fluorescence intensity is plotted, which shows good fitting degree. The concentration of 5fC base can be determined quantitatively by measuring the fluorescence intensity of 5fC reaction product in an unknown sample.

(2) Indirect Labeling of 5fC

Specific functional groups can be introduced into 5-formylcytosine by the reaction of the active methylene compound having a special functional group (i.e. active methylene compound containing a side-chain active group) with 5-formylcytosine, achieving indirect labeling of 5fC. In the case of fluorescent molecule, indirect labeling of 5fC is implemented by using the fluorescence emission spectrum of this fluorescent molecule under certain exciting light. Besides, azido or alkynyl can also be introduced, and then indirect labeling of 5fC is performed by further using the principle of click chemistry.

The click chemistry here mainly refers to the [3+2] cycloaddition reaction of azido with alkynyl or alkynyl derivatives.

2. Changing Related Enzymology Effect of 5-Formylcytosine

The chemical properties of 5fC bases can also be changed by the reaction in the method of the present invention, which means that specific labeling of 5-formylcytosine in DNA or RNA results in change in the chemical properties of 5-formylcytosine in biological samples, thus influencing the abilities of nucleic acid-binding proteins (such as nucleic acid polymerase, and restriction endonuclease) to identify and bind the 5fC-containing nucleic acids, and then the activities of related proteins to identify nucleic acid substrates can be influenced. Such a change can be used in special biological studies.

In an embodiment, the 5fC base on the substrate sequence for TaqαI restriction endonuclease is labeled with compound iv, and therefore the enzyme digestion reaction activity of TaqαI is influenced, such that TaqαI fails to digest the chemical-reaction-modified T/$C^{5f}$GA sequence.

The enzyme treatment effect is changed by the chemical modification of 5fC mentioned above, in which the enzyme used comprises various restriction endonucleases and DNA polymerase. The commercial companies which provide enzyme reagents includes but not limited to for example NEB, Thermo Scientific, TAKARA, Promega, Agilent and the like.

3. Specific Enrichment of 5fC

Specific functional groups are introduced into 5-formylcytosine by means of the reaction of the active methylene compound having a special functional group (selected from the above side-chain active group-containing active methylene compounds i, ii, iii, and iv) with 5-formylcytosine, and the chemical properties of such special functional groups are used to implement the specific enrichment of a nucleic acid molecule containing 5-formylcytosine. For example, azido is introduced into the active methylene compound, and click chemistry reaction with this azido is performed by using biotin-labeled alkynyl or alkynyl derivatives, such that the biotin label is indirectly introduced into 5-formylcytosine; and then by means of the specific binding between streptavidin and biotin, screening of nucleic acid molecule with 5-formylcytosine is implemented. On the contrary, alkynyl can also be introduced into the active methylene compound, click chemistry reaction with this alkynyl is performed by utilizing azido molecule with biotin label, and then the enrichment can be implemented in the same way above.

In a specific embodiment, 5fC is specifically labeled with an azido derivative of 1,3-indandione-compound AI, the obtained molecule is further labeled with biotin by means of click reaction, and then the specific binding between biotin and streptavidin is used to enrich the nucleic acid molecule containing 5fC. The same effect can also be achieved by using an azido derivative of ethyl acetoacetate, i.e. ethyl 6-azido-3-oxyhexanoate.

4. Detection of Distribution Information of 5fC in Genome

By means of the above method for specifically enriching 5fC, the detection of distribution information of 5fC in genome can be implemented. Through the specific labeling of 5fC base, the enrichment and purification of a genomic DNA fragment containing 5fC base is implemented. Then by means of sequencing and alignment with corresponding genome, the distribution information of 5-formylcytosine in genome such as, regulatory region, transcription initiation region, gene exon and intron regions, characteristic histone modification region and the like in gene can be analyzed.

The genomic DNA samples above can be derived from cell culture, animal tissue, animal blood, formalin-fixed tissue, paraffin-embedded tissue, and trace sample such as early development sample of embryo, single cell and the like.

5. Single-Base Resolution Sequencing of 5fC

The method of the present invention, i.e., the specific reaction between an active methylene group containing a side-chain active group and 5fC, can be used for single-base resolution detection of the 5fC position in the sequence of a nucleic acid sample.

The nucleic acid sample above refers to a genomic DNA sample or RNA sample, which can be derived from cell culture, animal tissue, animal blood, formalin-fixed tissue, paraffin-embedded tissue, and trace sample such as early development sample of embryo, single cell and the like.

Any technique using such reactions to carry out 5fC base sequencing can be applied to the present invention.

(1) 5fC Ring-Protecting Sodium Bisulfite Sequencing Technique

5fC ring-protecting sodium bisulfite sequencing technique is implemented through the reaction between compound i and 5-formylcytosine. The core of this technique lies in performing sodium bisulfite sequencing for the samples before and after the reaction with compound i respectively. 5fC site in the sample is read as T in sequencing before the reaction, while 5fC base is read as C by sequencing after the reaction for that 5fC base is "protected" by a conjugate structure enabling it to be resistant to sodium bisulfite treatment. By comparing these two sequencing results, T-C mismatching sites are found, and single-base resolution sequence information of 5fC can be identified.

The sodium bisulfite sequencing above refers to that nucleic acid is treated under a weak acid condition with high concentration sodium bisulfite, and cytosine (and the oxides thereof, i.e. 5-formylcytosine and 5-carboxylcytosine) is hydrolyzed to remove 4-amino, and finally converted to uracil. However, the two derivatives of cytosine, i.e. 5-methylcytosine 5mC and 5-hydroxymethylcytosine 5hmC will not be converted to uracil. In Polymerase Chain Reaction (PCR) amplification, uracil U is read as thymine T, and both the remaining 5mC and 5hmC are amplified into C. Further sequencing can determine whether a site read as C is 5mC or 5hmC.

In a specific embodiment, compound i is selected as diethyl malonate. 5fC base in the sequence is read as T in sodium bisulfite sequencing before the reaction, while the product of 5fC is read as C in sodium bisulfite sequencing after the reaction.

(2) Ring Formation Promoting 5fC to T Conversion Sequencing Technique

"Ring formation promoting 5fC to T conversion sequencing technique" can be implemented through the reaction between compound ii and 5-formylcytosine. The core of this technique lies in performing PCR amplification and sequencing for the samples before and after the reaction with compound ii respectively. 5fC site in the sample is not influenced before the reaction, and is read as cytosine C in sequencing; while 5fC site in the sample is read as thymine T in sequencing after the reaction, and therefore the sequencing result thereof is also shown as T. By comparing these two sequencing results, mutation sites of C-T are found, and single-base resolution sequence information of 5fC can be identified.

"Ring formation promoting 5fC to T conversion sequencing technique" can also be implemented through the reaction between compound iii and 5-formylcytosine. The process thereof is similar with that when using compound ii, which comprises performing PCR amplification for the samples before and after the reaction with compound iii respectively. 5fC site in the sample is read as C before the reaction, while 5fC site in the sample is read as T after the reaction. By comparing the two sequencing results, particular sequence information of 5fC can be identified.

As for the two sequencing methods in (1) and (2) before, the related particular commercial sequencing platform can be selected from any of the followings:

1) the first generation dideoxy base sequencing method, in which the commercial sequencing platforms that can be used include a series of instruments for the first generation sequencing platform from ABI;

2) the second generation high-throughput sequencing technique, in which the commercial sequencing platforms that can be used include: a series of sequencing platforms from Illumina (former Solexa), including but not limited to, Miseq, Hiseq 2000, Hiseq2500, NextSeq 500, Hiseq X, etc.; sequencing platforms using pyrosequencing method from Roche (fainter 454), for example, including but not limited to GS FLX; and SOLiD sequencing platforms from ABI, for example, including but not limited to SOLiD 5500;

3) the third generation single molecule sequencing technique, in which the commercial sequencing platforms that can be used include: SMRT sequencing platforms from Pacific Bioscience, for example, including but not limited to SMRT RSII; nanopore single molecule sequencing platforms from Oxford Nanopore Technologies, such as Mni-ION platform; HeliScope platform from Helicos Biosciences.

(3) The Third Generation Single Molecule Sequencing Based on Chemical Modification of 5fC The target bases are directly detected through the modification to the chemical structure of 5fC base with compound i, ii, or iii, and the third generation single molecule sequencing technique. By changing the chemical properties for protein to identify the modified 5fC base, the kinetic parameter of the binding of protein to base during the third generation single molecule sequencing are influenced, such that the base is distinguished from other naturally existing bases, thus directly identifying the position of the target 5fC bases.

The third generation single molecule sequencing platform here can be selected from SMRT sequencing platforms from Pacific Bioscience, or nanopore single molecule sequencing platforms from Oxford Nanopore Technologies. When using SMRT sequencing platform, the amplification efficiency of polymerase is influenced after the modification to the chemical structure of 5fC base with compound i, ii or iii, such that the kinetic parameter of amplification are influenced, and the positions of 5fC are identified. When using nanopore single molecule sequencing platform, the kinetic parameter of the binding of nanopore protein to base are influenced after the modification to the chemical structure of 5fC base with compound i, ii or iii. By measuring this kinetic parameter, it can be determined that whether the base is a modified 5fC base.

6. Kits for 5-Formylcytosine Sequencing.

(1) Kit 1 for "5fC Ring-Protecting Sodium Bisulfite Sequencing Technique"

By means of the reaction method for labeling 5-formylcytosine with azido-containing compound i, kit 1 for single-base resolution analysis of sequence information of 5-formylcytosine in a nucleic acid sample is designed. Based on the specific reaction between ethyl 6-azido-3-oxyhexanoate and 5fC, biotin is introduced to 5fC through click chemistry reaction, so as to perform selective enrichment of 5fC. In combination with sodium bisulfite sequencing technique, the sequencing results before and after the treatment with compound ethyl 6-azido-3-oxyhexanoate are compared to identify the positions of 5fC base, achieving the "5fC ring-protecting sodium bisulfite sequencing technique". Kit 1 mainly comprises the following 4 modules:

Module 1: a 5fC reaction module, comprising a reagent of ethyl 6-azido-3-oxyhexanoate, and corresponding reaction solution. This module is used to react with 5fC base in nucleic acid sample, to label 5fC base with azido.

Module 2: a selective enrichment module, comprising magnetic beads specifically binding to biotin, a screening buffer, and a reagent which selectively reacts with azido and contains biotin modification.

This module is used to perform a click chemistry [3+2] cycloaddition reaction with the azido labeled in nucleic acid sample, such that 5fC base is further labeled with biotin. Further, by means of the binding of biotin to the streptavidin coupled to the magnetic beads, the nucleic acid sample fragments containing 5fC base are separated and purified with a magnetic frame.

Module 3: a sodium bisulfite treatment module, comprising a sodium bisulfite treating reagent and related recovering materials.

This module is used to react with the enriched nucleic acid sample fragment, such that normal cytosines and remaining 5-carboxylcytosines are deaminated and hydrolyzed into uracil U.

Module 4: a specific PCR amplification module, comprising a specific DNA polymerase and a reaction system screened for the reaction product of 5fC.

This module is used to amplify the labeled and sodium bisulfite treated nucleic acid sample, so as to perform high-throughput sequencing.

(2) Kit 2 for "Ring Formation Promoting 5fC to T Conversion Sequencing Technique"

By means of the reaction method for labeling 5-formylcytosine with azido-containing compound iv, kit 2 for single-base resolution analysis of sequence information of 5-formylcytosine in a nucleic acid sample is designed. In an example, based on the specific reaction between compound AI and 5fC, biotin is introduced to 5fC through click chemistry reaction, so as to perform selective enrichment of 5fC. Samples before and after the treatment of compound iv are PCR amplified and sequenced. By comparing the sequencing results, the sequence position of 5fC base can be identified, achieving the "ring formation promoting 5fC to T conversion sequencing technique". Kit 2 mainly comprises the following 3 modules:

Module 1: a 5fC reaction module, comprising a reagent compound AI, (5-(2-azidoethyl)-1,3-indandione), and corresponding reaction solution.

This module is used to react with 5fC base in nucleic acid sample to label 5fC base with azido. Module 2: a selective enrichment module, comprising magnetic beads specifically binding to biotin, a screening buffer, and a reagent which selectively reacts with azido and contains biotin modification.

This module is used to perform a click chemistry [3+2] cycloaddition reaction with the azido labeled in nucleic acid sample, such that 5fC base is further labeled with biotin. Further, by means of the binding of biotin to the streptavidin coupled to the magnetic beads, the nucleic acid sample fragments containing 5fC base are separated and purified with a magnetic frame.

Module 3: a specific PCR amplification module, comprising a specific DNA polymerase and a reaction system screened for the reaction product of 5fC.

This module is used to amplify the enriched nucleic acid sample, so as to perform high-throughput sequencing. At the same time, the original 5fC site is allowed to be read as T in PCR amplification, and thus a mutation point is introduced, achieving the "ring formation promoting 5fC to T conversion sequencing technique".

(3) Kit 3 for "Ring Formation Promoting 5fC to T Conversion Sequencing Technique"

By means of the reaction method for labeling 5-formylcytosine with compound ii or iii, kit 3 for single-base resolution analysis of sequence information of 5-formylcytosine in a nucleic acid sample is designed. The selective enrichment is performed with a published specific antibody for 5-formylcytosine (Li Shen, et al., Cell, 2013, 153:692-706). Then malononitrile is reacted with 5fC, and the conversion from 5fC to T is resulted by PCR. By comparing the sequencing results of the amplified products, the position of 5fC base in the sequence can be identified, thus achieving the "ring formation promoting 5fC to T conversion sequencing technique". Kit 3 mainly comprises the following 3 modules:

Module 1: a module for immunoprecipitation enrichment of 5-formylcytosine, comprising a 5fC antibody and corresponding reaction buffer for DNA immunoprecipitation test.

This module is used to directly enrich the nucleic acid sample fragment containing 5fC base.

Module 2: a 5fC reaction module, comprising a reagent of malononitrile (compound ii) or 1,3-indandione (compound iii), and corresponding reaction solution.

This module is used to react with 5fC base in the nucleic acid sample.

Module 3: a specific PCR amplification module, comprising a specific DNA polymerase and reaction system screened for the reaction product of 5fC.

This module is used to amplify and enrich the malononitrile treated nucleic acid sample, so as to perform high-throughput sequencing. At the same time, the original 5fC site is allowed to be read as T in PCR amplification, and thus a mutation point is introduced, achieving the "ring formation promoting 5fC to T conversion sequencing technique".

(4) Kit 4 for Single Molecule Sequencing Based on Labeling of 5fC

By means of the reaction method for labeling 5-formylcytosine with azido labeled compound i or iii (including compound iv), in combination with the third generation single molecule sequencing platform, kit 4 for single-base resolution analysis of sequence information of 5-formylcytosine in a nucleic acid sample is designed. Based on the selective enrichment of DNA fragment containing 5fC base with ethyl 6-azido-3-oxyhexanoate or compound AI, the third generation single molecule real-time detection platform is further used to find the position having a special kinetic parameter, and identify the 5fC modified position, achieving single molecule real-time detection of sequence information of 5fC bases. Kit 4 mainly comprises the following 2 modules:

Module 1: a 5fC reaction module, comprising a reagent of ethyl 6-azido-3-oxyhexanoate (compound i) or compound AI (5-(2-azidoethyl)-1,3-indandione, compound iv), and corresponding reaction solution.

This module is used to react with 5fC base in nucleic acid sample, so as to label 5fC base with azido.

Module 2: a selective enrichment module, comprising magnetic beads specifically binding to biotin, a screening buffer, and a reagent which selectively reacts with azido and contains biotin modification.

This module is used to perform a click chemistry [3+2] cycloaddition reaction with the azido labeled in genome, such that 5fC base is further labeled with biotin. Further, by means of the binding of biotin to the streptavidin coupled to the magnetic beads, the nucleic acid sample fragments containing 5fC base are separated and purified with a magnetic frame.

The nucleic acid sample targeted by kits 1, 2, 3, and 4 above refer to genomic a DNA sample or RNA sample, which can be derived from cell culture, animal tissue, animal blood, formalin-fixed tissue, paraffin-embedded tissue, and trace sample such as early development sample of embryo, single cell and the like.

7. 5fC Labeling Method and Application of Related Compounds in the Aspect of Molecule Diagnosis The above specific enrichment methods for 5fC, and related active methylene compounds containing a specific chemical label are used in the molecule diagnosis involving 5-formylcytosine in biological samples. The changes in activities and expression quantities of 5-formylcytosine related proteins produced in cells such as TET protein, TDG for excision of 5-formylcytosine and the like will influence the content and sequence distribution of 5-formylcytosine in the genome. The changes in the content and sequence distribution of 5-formylcytosine in the biological samples are detected by using the above related labeling, detection, and sequencing methods for 5-formylcytosine. Thus, reference data can be provided for disease diagnosis and pathology indications such as pathological changes and histological changes, which is beneficial for clinical diagnosis.

The present invention is further described through the following 8 particular examples, for the purpose of better understanding of the contents of the present invention. The contents of the present invention, however, are not limited to the examples illustrated below. All the reagents and solvents used in the examples are bought from commercial companies, unless otherwise specified.

The DNA Sequences Involved in the Tests of the Present Invention

| Oligo ID NO. | Sequence (5'-3') | Notes | SEQ ID No. |
|---|---|---|---|
| 1 | AGATC$^{5f}$GTAT | 5fC-9mer | 22 |
| 2 | AGATCGTAT | C-9mer | 23 |
| 3 | AGATC$^{5m}$GTAT | 5mC-9mer | 24 |
| 4 | AGATC$^{5hm}$GTAT | 5hmC-9mer | 25 |
| 5 | AGATC$^{5ca}$GTAT | 5caC-9mer | 26 |
| 6 | CCTCACCATCTCAACCAATATTATATTATGTCTACACGTTC$^{5f}$GC$^{5f}$GTTCCGTGTTATAATATTGAGGGAGAAGTGGTGA | Oligo NO.6 Forward | 1 |
|   | TCACCACTTCTCCCTCAATATTATAACACGGAACG*CG*AACGTGTAGACATAATATAATATTGGTTGAGATGGTGAGG | Oligo NO.6 Reverse | 2 |
| 7 | CCCTTT TATTATTTTAATTAATATTATATT | Model-BS-F | 3 |
| 8 | CTCCGACATTATCACTACCATCAACCACCCATCCTACCTGGACTACATTCTTATTCAGTATTCACCACTTCTCCCTCAAT | Model-R | 4 |
| 9 | CTCCGACATTATCACTACCA | Model-Seq R sequencing primer | 5 |
| 10 | CATGAGTGCCCTCAGCAGTAAGTAACTGACCAGATCTCTCGTGCCTCTTGAGGCTACTGAGTTATCCAACCTTTAGGAGCCATGCATCGATAGCATCCGC$^{5f}$CACAGGCAGTGAGGCTACTGAGTCATGCACGCAGAAAGAAATAGC | qPCR-5fC-M dsDNA | 6 |
| 11 | ATTCACTCCCACTGAGACTGTGGATCAGGCCAACATACATGCCTTCAGTAACTGACCAGATCTCTTAGTTCTCTTGAGGCTACTGAGTTAGAATGGCAGAGTCAAGGAGC<br>Obtained by PCR amplification, comprising 100% dATP, 100% dTTP, 100% dGTP, 70% dCTP, 15% d5mCTP, 10% d5hmCTP, 5% d5caCTP | qPCR-Ctl dsDNA | 7 |
| 12 | CTACGCAAACTGGCTGTCAAAGTAACTGACCAGATCTCTCGGCTCTCTTGAGGCTACTGAGTTATCATGGACGCTACCTCACAG | qPCR-Ref dsDNA | 8 |
| 13 | CATGAGTGCCCTCAGCAGTA | qPCR-M-F | 9 |
| 14 | TCCAACCTTTAGGAGCCATG | qPCR-M-R | 10 |
| 15 | AGGCCAACATACATGCCTTC | qPCR-Ctl-F | 11 |
| 16 | GAATGGCAGAGTCAAGGAGC | qPCR-Ctl-R | 12 |
| 17 | CTACGCAAACTGGCTGTCAA | qPCR-Ref-F | 13 |

-continued

| Oligo ID NO. | Sequence (5'-3') | Notes | SEQ ID No. |
|---|---|---|---|
| 18 | CTGTGAGGTAGCGTCCATGA | qPCR-Ref-R | 14 |
| 19 | CCTCACCATCTCAACCAATATTATATTACGCGTATATC$^{5f}$G C$^{5f}$GTATTTCGCGTTATAATATTGAGGGAGAAGTGGTGA | 76mer 5fCx.2 | 15 |
| 20 | CCTCACCATCTCAACCAATA | Model-F | 16 |
| 21 | CCTCACCATCTCAACCAATATTATATTACGCGTATATC$^{5f}$G CGTATTTCGCGTTATAATATTGAGGGAGAAGTGGTGA | 76mer 5fCx1 | 17 |
| 22 | CCTCACCATCTCAACCAATATTATATTAGTATTTC$^{5f}$GATTAC GCGTTATTATATTGAGGGAGAAGTGGTGA | Oligo NO.22 Forward | 18 |
|  | TCACCACTTCTCCCTCAATATAATAACGCGTAATCGAAATA CTAATATAATATTGGTTGAGATGGTGAGG | Oligo NO.22 Reverse | 19 |
| 23 | CCTCACCATCTCAACCAATATTATATTAGTATTTCGATTACG CGTTATTATATTGAGGGAGAAGTGGTGA | Oligo NO.23 Forward | 20 |
|  | TCACCACTTCTCCCTCAATATAATAACGCGTAATCGAAATA CTAATATAATATTGGTTGAGATGGTGAGG | Oligo NO.23 Reverse | 21 |

All the oligomeric nucleotide chains with modified base used in the experiments were synthesized by using ABI EXPEDIATE nucleic acid solid-phase synthesizer. The phosphoramidite monomers used for synthesis were bought from Glen Research, USA. The oligomeric nucleotide chains containing only normal bases used in the experiments were synthesized by Sangon Biotech (Shanghai) Co., Ltd.

Example 1

Synthesis of the Representative Compounds of Compounds I, II, and III

The artificially synthesized 9-base oligomeric nucleotide chain containing 5fC base Oligo NO.1 was reacted with the representative compounds i-1, ii-1, and iii-1 of 3 kinds of compounds i, ii, and iii, resulting in 3 representative product compound I-1, II-1, and 111-3 of 3 structures I, II, and III. In the reaction, the representative compound of compound i is either ethyl acetoacetate or methyl acetoacetate; the representative compound of compound ii is malononitrile; and the representative compound of compound iii is 1,3-indandione.

The particular reaction route was as below.

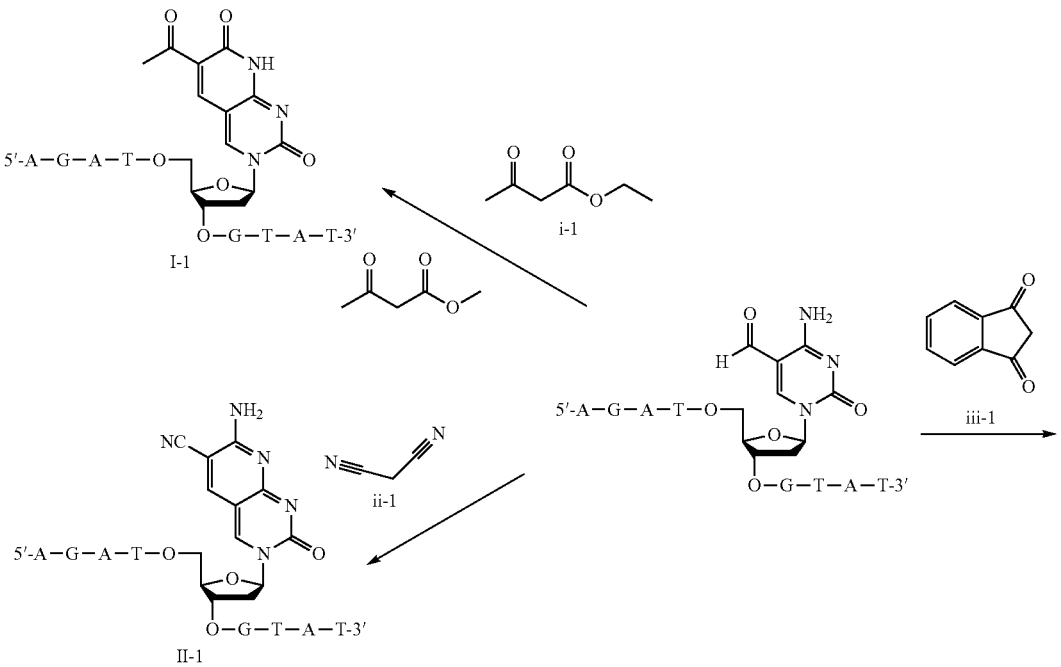

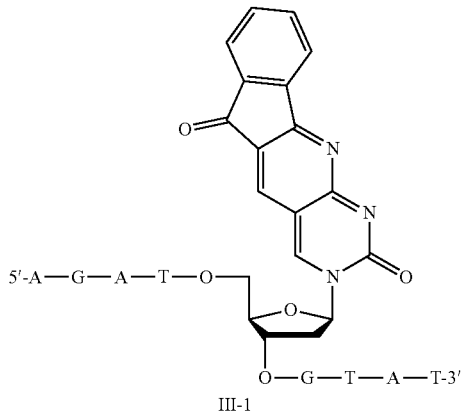

III-1

Compound i-1 was the representative compound, ethyl acetoacetate or methyl acetoacetate. An appropriate amount of Oligo NO.1, i.e. 5fC-9mer DNA oligomeric nucleotide chain, was dissolved in an alkaline methanol solution, then much excessive moles of ethyl acetoacetate or methyl acetoacetate was directly added, and the reaction was performed under agitation at 37° C. for 24 h after mixing homogeneously, obtaining the same compound I-1. In the reaction, the active methylene at 2-position of ethyl acetoacetate or methyl acetoacetate was condensed with formyl of 5fC, and at the same time an intramolecular reaction occurred, during which the 4-amino in the cytosine ring replaced the ethanol/methanol portion in the ester bond, thereby resulting in compound I-1 by ring formation. The MALDI-TOF mass spectrum identification showed that no peak of raw materials remained, m/z$^{(ob)}$: 2763.5→m/z$^{(ob)}$: 2829.8/2829.5 (as shown in A, B, and C of FIG. 1).

Compound ii-1 was the representative compound, malononitrile. An appropriate amount of Oligo NO.1, i.e. 5fC-9mer DNA oligomeric nucleotide chain, was dissolved in an weak acidic aqueous solution, much excessive moles of high-concentration aqueous stock solution of malononitrile was simultaneously added, and the reaction was performed under agitation at 37° C. for 24 h after mixing homogeneously, obtaining compound II-1. In the reaction, the active methylene of malononitrile was condensed with 5-formyl of 5fC, and then the 4-amino in the cytosine formed a ring together with the cyano of malononitrile through an intramolecular addition reaction, resulting in target compound II-1. The MALDI-TOF mass spectrum identification showed that no peak of raw materials remained, m/z$^{(ob)}$: 2763.5→m/z$^{(ob)}$: 2812.5 (as shown in A and D of FIG. 1).

Compound iii-1 was the representative compound, 1,3-indandione. The reaction of 1,3-indandione with 5fC DNA can be accomplished in an alkaline methanol solution or a weak acidic aqueous solution. An appropriate amount of Oligo NO.1, i.e. 5fC-9mer DNA oligomeric nucleotide chain, was dissolved, much excessive moles of 1,3-indandione in the form of yellow solid was simultaneously added to be dissolved (in an alkaline methanol solution) or reach saturation (in a weak acidic aqueous solution), and the reaction was performed under agitation at 37° C. for 24 h after mixing homogeneously, obtaining compound III-1. In the reaction, the active methylene of malononitrile was condensed with 5-formyl of 5fC, and the 4-amino in the cytosine formed a ring together with the cyano of malononitrile through an intramolecular addition reaction, resulting in target compound III-1. The MALDI-TOF mass spectrum identification showed that no peak of raw materials remained, m/z$^{(ob)}$: 2763.5→m/z$^{(ob)}$: 2874.7 (as shown in A and E of FIG. 1).

The results of MALDI-TOF mass spectrum in FIG. 1 showed that no peak of raw materials was detected, which indicates extremely high reaction efficiency.

The reaction provided by the present invention has excellent selectivity. The reaction is specific for 5fC base only, and no side reaction with other cytosines or cytosine derivatives occurs. As shown in FIG. 2, malononitrile as representative was reacted with other 4 cytosines (C, 5mC, 5mhC, and 5caC) containing DNA sequences (Oligo NO.2, Oligo NO.3, Oligo NO.4, and Oligo NO.5, respectively). MALDI-TOF mass spectrum identification showed that the other cytosines or cytosine derivatives were not reacted, and the corresponding increase in molecular weight was only observed for 5fC-9mer DNA sequence after reaction (the secondary peak in group of 5hmC was attributed to incompletely purified sample). This demonstrated excellent reaction selectivity.

Example 2

Implementing "5fC Ring-Protecting Sodium Bisulfite Sequencing Technique" with Diethyl Malonate Diethyl malonate belongs to the active methylene of compound i. The target compound 1-2 can be obtained through a two-step condensation reaction of diethyl malonate with 5fC base in an alkaline methanol solution (as shown in the schematic diagram below). The process of the reaction of Oligo NO.1, i.e. 5fC-9mer DNA oligomeric nucleotide chain with diethyl malonate is as follows: an appropriate amount of DNA oligomeric nucleotide chains was dissolved in an alkaline methanol solution, then much excessive moles of diethyl malonate was directly added, and the reaction was performed under agitation at 37° C. for 24 h after mixing homogeneously, obtaining compound I-2. In the reaction, the active methylene at 2-position of diethyl malonate was condensed with the formyl of 5fC, and at the same time, an intramolecular reaction occurred, during which the 4-amino in the cytosine ring replaced the ethanol portion of the ester bond; and at the same time, a transesterification reaction of the ester bond which did not participate in the ring formation occurred in the alkaline methanol solution to form a methoxyl carbonyl group, producing compound I-2 through ring formation. The MALDI-TOF mass spectrum identification indicated that there is no peak of raw materials remained, m/z$^{(ob)}$: 2763.5→m/z$^{(ob)}$: 2845.4 (as shown in A and F of FIG. 1).

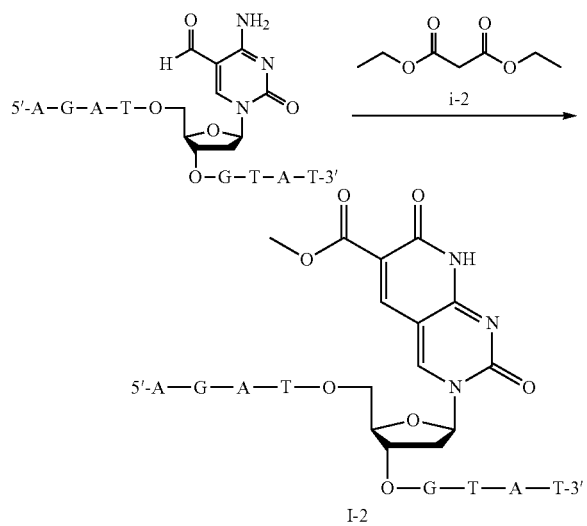

A double-stranded DNA sequence Oligo NO.6 containing two 5fC bases and with 77 bases in length was reacted with diethyl malonate. In Oligo NO.6 sequence, the forward chain comprises two 5fC bases, such as 5fC base as shown in bold in the sequence (5-C$^{5f}$GC$^{5f}$G-3), and the reverse chain does not comprise 5fC base, of which the sequence corresponding to 5fC base is G (5-CG*CG*-3). After the treatment of sodium bisulfite, PCR amplification was performed on two primers of Oligo NO.7 and Oligo NO.8. The reverse sequencing primer Oligo NO.9 was used when sequencing. Thus, the G* signals of sequence 5-CG*CG*-3 in the read results were corresponding to 5fC signals. The reaction conditions were the same as set forth. After evaporating methanol to dryness, the reaction product was recovered through ethanol precipitation.

The recovered DNA samples were amplified directly through PCR reaction or amplified through PCR after treating the sample with EpiTect Fast Bisulfite Conversion Kit from QIAGEN. The reaction product was then sequenced to identify whether it is resistant to the treatment of sodium bisulfite. As shown in the sequencing results in FIGS. 3A and 3B, when the product was directly amplified and sequenced after the reaction with diethyl malonate, cytosines or 5fC bases were correspondingly read as significant guanine G signals. However, after treatment with sodium bisulfite, normal cytosines in the sample sequence were converted to uracil U, which were amplified into thymine T through PCR, and thus read as adenine A signals. However, the products 5fC* after the reaction with diethyl malonate were resistant to the sodium bisulfite treatment, remained to pair with cytosine C bases during PCR process, and thus were read as guanine G signals in sequencing. This means that ring formation reaction protected the 4-amino of cytosine, and did not influence such cytosine to be read as C during normal PCR process. During the sodium bisulfite treatment, the protected 5fC was not deaminated and hydrolyzed. However, other normal cytosines were deaminated and hydrolyzed during the sodium bisulfite treatment, and read as T in sequencing. By comparing the sodium bisulfite sequencing results before and after the reaction, the single-base resolution sequence positions of 5fC can be identified (FIGS. 3A and 3B).

In this method, the 4-amino of cytosine was protected by ring formation reaction, such that the cytosine was prevented from being deaminated and hydrolyzed. In comparison with the case that the 5fC position before ring formation reaction can be deaminated and hydrolyzed and therefore read as T in sequencing, the position of 5fC base in the sequence can be identified. This method can be called as "5fC ring formation-protecting sodium bisulfite sequencing technique".

Example 3

Specific Enrichment of Nucleic Acid Containing 5fC Base with the Representative Compound AI of Type iv (formula iv-1)

The reactive region of 1,3-indandione is the methylene between the carbonyl groups in the 5-membered ring. Thus, the modifications at positions 3, 4, 5, and 6 of benzene ring structure will not have significant effect on the properties of the compound. Therefore, 5-(2-azidoethyl)-1,3-indandione (compound AI) was synthesized for specifically enriching nucleic acid containing 5fC bases.

The synthesis route of 5-(2-azidoethyl)-1,3-indandione (compound AI) is as below.

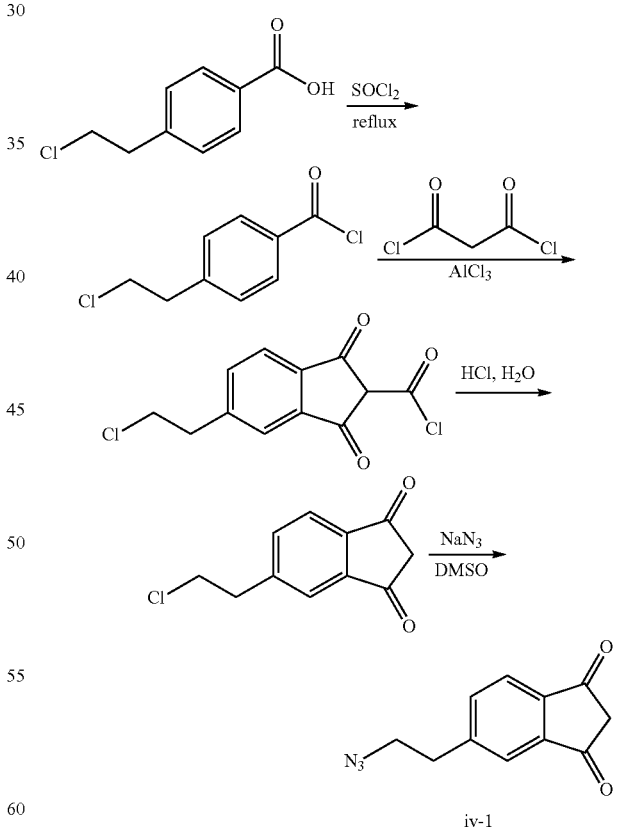

Synthesis of 4-(2-chloroethyl)-benzoyl chloride 4-(2-chloroethyl)-benzoic acid (10 g, 108 mmol) was mixed with 50 mL SOCl$_2$, several drops of DMF was added, the mixture was heated and refluxed for 12 h, and then excessive SOCl$_2$ was evaporated, resulting in yellow liquid (10.8 g, 96%). This liquid was directly used in the next reaction step.

Synthesis of 5-(2-chloroethyl)-1,3-indandione (5-(2-chloroethyl)-1H-indene-1,3(2H)-dione)

AlCl$_3$ (14 g, 106 mmol, 1 eq.) and 200 ml CH$_2$Cl$_2$ were added into a 500 mL dried 2-necked flask. 4-(2-chloroethyl)-benzoyl chloride (21.6 g, 106 mmol) was added into CH$_2$Cl$_2$ solution under the protection of nitrogen. Then redistilled malonyl dichloride (16.5 g, 117 mmol, 1.1 eq.) was dropped slowly into the solution at 0° C., resulting in dark brown liquid. The reaction was performed at room temperature for 12 h. After the reaction, the solution was poured into ice, followed by adding HCl solution (10%, 250 mL) and stirring vigorously for 1 h. Then the solution was extracted with CHCl$_3$ (3×400 mL). The extract was dried with anhydrous sodium sulfate, concentrated, subjected to column chromatography on silica gel, and eluted with petroleum ether/dichloromethane 2:1, resulting in light yellow solid (7.9 g, 36%). 1H NMR (300 MHz, CDCl3) δ 7.93 (d, J=7.8 Hz, 1H), 7.83 (s, 1H), 7.71 (d, J=7.8 Hz, 1H), 3.80 (t, J=6.6 Hz, 2H), 3.25 (t, J=6.6 Hz, 2H), 3.24 (s, 2H).

Synthesis of 5-(2-Azidoethyl)-1,3-Indandione (5-(2-Azidoethyl)-1H-Indene-1,3(2H)-Dione, i.e. AI)

NaN$_3$ (2.3 g, 36 mmol, 2 eq.) was dissolved in 100 mL dried DMSO, and 5-(2-azidoethyl)-1,3-indandione (3.7 g, 18 mmol) was added. The reaction was performed at 80° C. for 20 min. After the reaction, 300 mL water was added into the solution. Then the solution was extracted with diethyl ether (3×400 mL). The extract was dried with anhydrous sodium sulfate, concentrated, subjected to column chromatography on silica gel, and eluted with petroleum ether/dichloromethane 1:1, resulting in light yellow solid (680 mg, 18%). 1H NMR (300 MHz, CDCl3) δ 7.94 (d, J=7.8 Hz, 1H), 7.82 (s, 1H), 7.70 (d, J=7.8 Hz, 1H), 3.62 (t, J=6.6 Hz, 2H), 3.24 (s, 2H), 3.06 (t, J=6.6 Hz, 2H), 13C NMR (75 MHz, CDCl3) δ 197.6, 197.1, 147.4, 144.1, 142.4, 136.7, 123.8, 123.4, 51.9, 45.6, 35.9; MS(ESI) [M+H]$^+$, 216.2.

Figure 4:
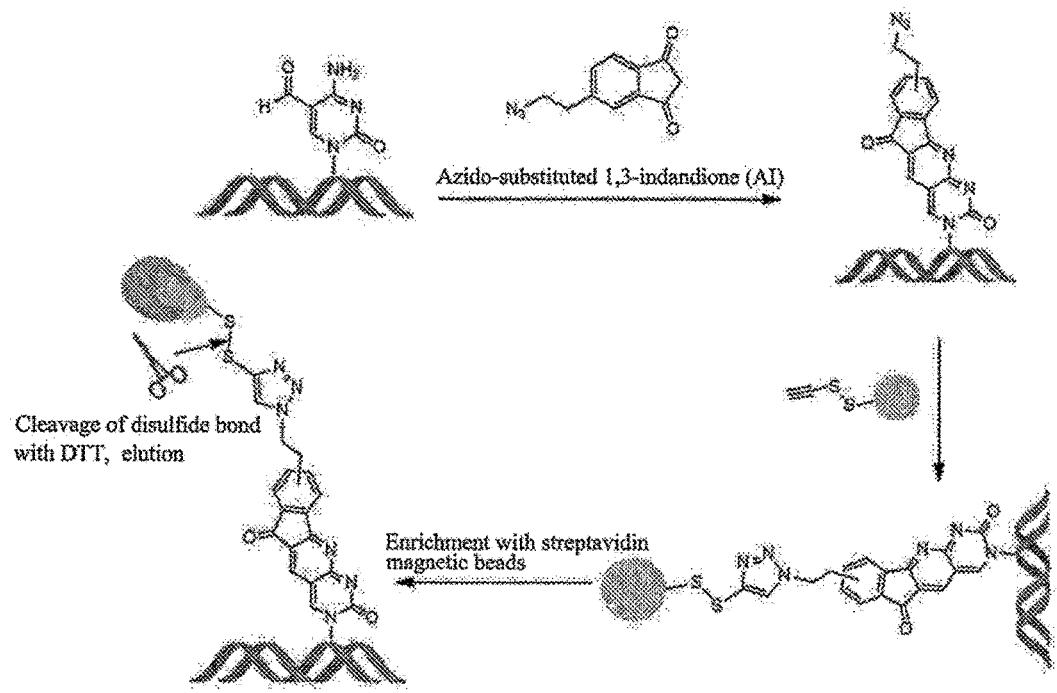
FIG. 4 is a flow chart of specifically enriching a nucleic acid containing a 5fC base with compound AI.
Figure 5:
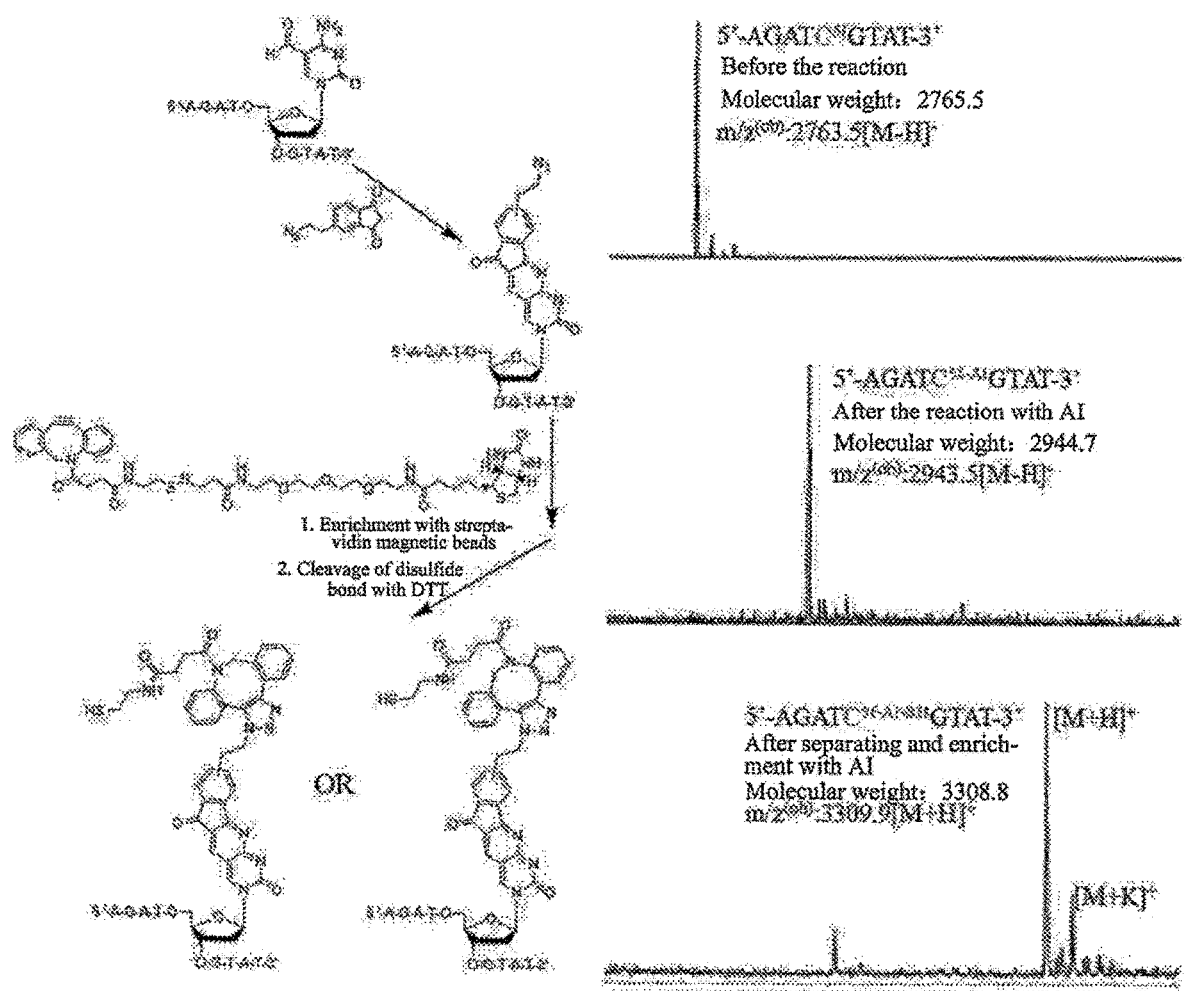
FIG. 5 is a flow chart for specifically enrichment with compound AI (left) and MALDI-TOF detection spectra (right) in example 3.

The specific reaction between the synthesized compound AI and nucleic acid sequence containing 5fC can be used to selectively separating and enriching DNA samples containing 5fC base. The process was as shown in FIG. 4, the 5fC base in a nucleic acid sample was reacted with the compound AI, such that an azido was specifically introduced. A biotin with disulfide linkage was further specifically introduced into the reaction product through the Click-Chemistry reaction between the azido and the alkynyl. In this way, through the two-step reaction, a biotin group was introduced into the position of 5fC base selectively and efficiently. Then, selective enrichment was carried out by utilizing the strong binding between streptavidin and biotin, and thus the DNA sequences containing 5fC were separated for the next operation such as sequencing analysis and the like. The MALDI-TOF mass spectrometry of the products obtained from respective steps of the reaction of Oligo NO.1 containing single 5fC with the compound AI, as shown in FIG. 5, exhibiting a high efficiency of the reaction.

Three artificially synthesized double-stranded DNA samples were incorporated into mouse embryonic stem cell genomic DNA samples in a portion of 2 pg/(1 μg gDNA). The samples were enriched through the experimental process above. The enrichment effect was detected by real time fluorescent quantitative PCR. The three sequences used were respectively: Oligo NO.10, comprising one 5fC site, for which Oligo NO.13/14 primer pair was used during qPCR; Oligo NO.11, a control sequence, obtained by PCR, comprising 100% dATP, 100% dTTP, 100% dGTP, 70% dCTP, 15% d5mCTP, 10% d5hmCTP, 5% d5caCTP, and comprising no 5fC, for which Oligo NO.15/16 primer pair was used during qPCR; and Oligo NO.12, a reference sequence, only comprising four kinds of basic bases, for which Oligo NO.17/18 primer pair was used during qPCR. The relative enrichment degree was calculated using "ΔCt" method.

Figure 6:
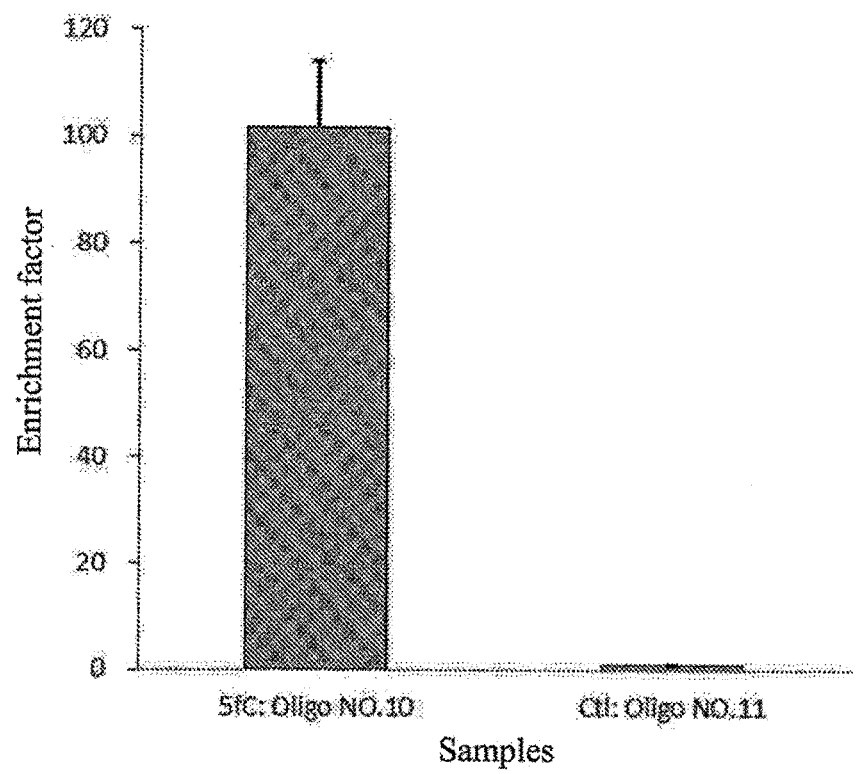
FIG. 6 shows the efficiency of enriching a DNA containing a 5fC base with compound AI in example 3.

The enrichment results were as shown in FIG. 6. It can be seen that, the DNA fragment containing 5fC can be selectively enriched with the compound AI. The enrichment degree for the DNA sequence containing only single 5fC base can be up to about 100 times. However, in the control group, the DNA sequence containing 15% 5 mC, 10% 5 hmC, or 5% 5 caC base was not enriched.

Figure 7:
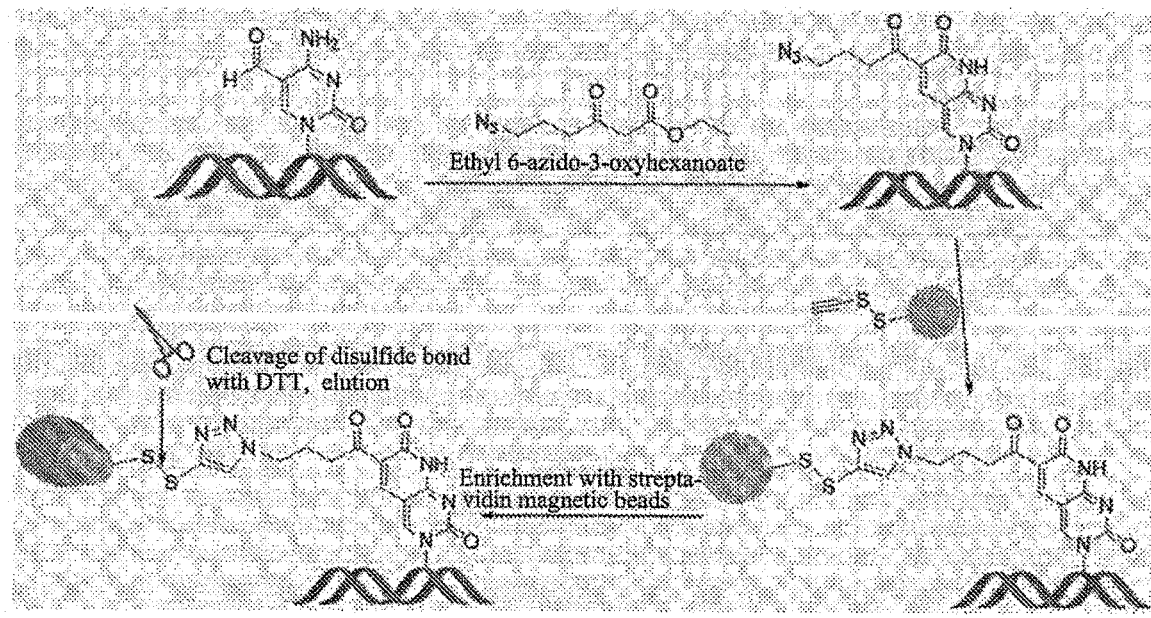
FIG. 7 is a flow chart of specifically enriching a nucleic acid containing a 5fC base with 6-azido-3-oxyethyl hexanoate.

Similar enrichment process can also be implemented with ethyl 6-azido-3-oxyhexanoate. As shown in FIG. 7, ethyl 6-azido-3-oxyhexanoate specifically reacted with a nucleic acid containing 5fC in an alkaline methanol solution, such that the nucleic acid containing 5fC was labeled with an azido. An affinity group, such as biotin, was further introduced into the nucleic acid by means of the click reaction between alkynyl and azido. The affinity group enabled the enrichment and separation of the nucleic acid containing 5fC.

Example 4

Implementing of "Ring Formation Promoting 5fC to T Conversion Sequencing Technique" with 1,3-Indandione and the Derivatives Thereof 1,3-indandione belongs to the representative compounds of compound iii of the present invention. A DNA sequence Oligo NO.19 containing two 5fC bases and with 76 bases in length was reacted with a derivative of 1,3-indandione-compound AI (see example 3 for the synthesis route and application thereof). The used sequence comprises two 5fC bases (5-C$^{5f}$GC$^{5f}$G-3). The sample before or after the reaction was amplified directly with Oligo NO.8 and Oligo NO.20. The amplified product was also sequenced with Oligo NO.9. Because of the reverse sequencing primer used, the G* signals of the sequence 5-CG*CG*-3 in the sequencing result were corresponding to the signals for 5fC sites. The reaction conditions were the same as set forth. The reaction product was recovered through ethanol precipitation.

Figure 8A:
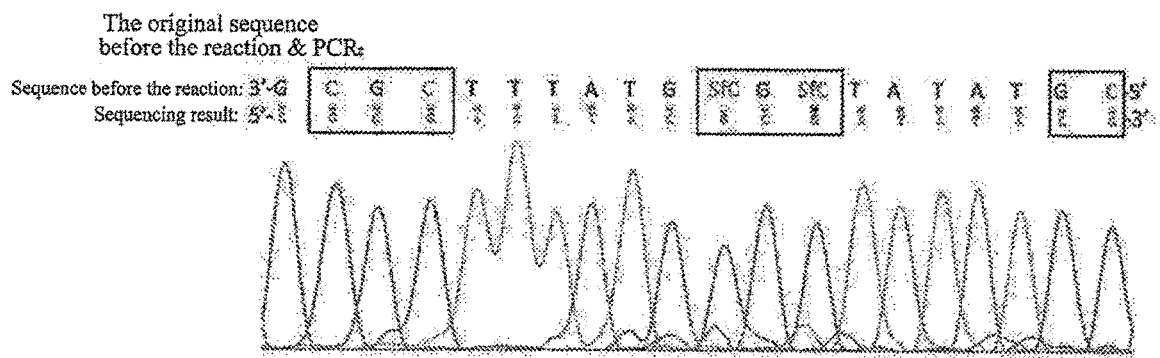
FIGS. 8A and 8B are respectively the sequencing results obtained before and after the reaction with compound AI in example 4, which show that "ring formation promoting 5fC to T conversion sequencing technique" is implemented with compound AI, wherein 5fC* represents the product obtained after the reaction of 5fC.
Figure 8B:
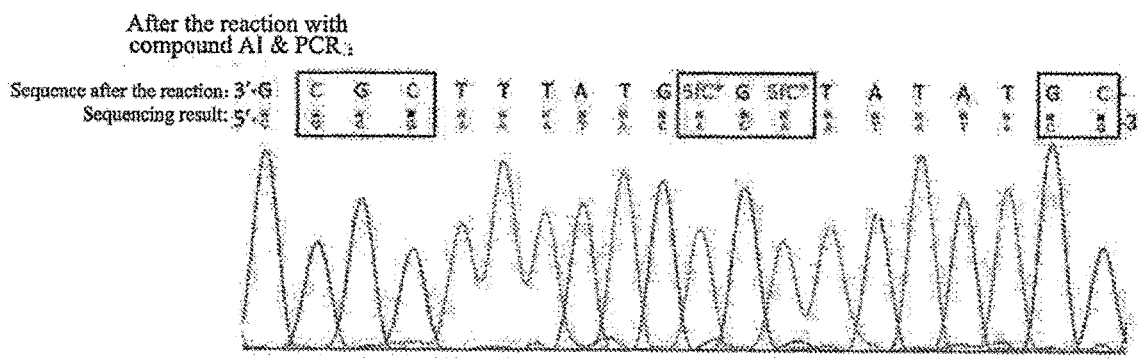

The "ring formation promoting 5fC to T conversion sequencing technique" was implemented with compound AI. The result thereof was as shown in FIGS. 8A and 8B. Before the reaction with compound AI, the two 5fC bases were read as guanine G signals. After the reaction, the two 5fC base positions were read as thymine T during PCR amplification. Thus, when using reverse sequencing primer, 5fC position was read as adenine A signal, and the regions corresponding to other cytosines were not influenced. By comparing the sequence information before and after the reaction, C-T mutation signal (forward primer sequencing) or G-A mutation signal (reverse primer sequencing) was found to be the position of 5fC base. In this way, single base resolution sequence information of 5fC in the genome can also be easily detected.

In this method, 5fC was reacted the compound AI, such that the reaction product of 5fC was read as thymine T during PCR amplification. By stably reading out the C-T mismatched sites through comparing the results before and after the reaction, the sequence position of 5fC can be directly identified. Such 5fC sequencing methods can be called as "ring formation promoting 5fC to T conversion sequencing technique".

Example 5

Implementing of "Ring Formation Promoting 5fC to T Conversion Sequencing Technique" by Means of Malononitrile Reaction Malononitrile belongs to the representative compounds of compound ii of the invention. A DNA sequence Oligo NO.21 containing single 5fC base and with 76 bases in length was reacted with malononitrile. The used sequence comprises only one 5fC base (5-$C^{5f}$GCG-3). The sample before or after the reaction was amplified directly with Oligo NO.8 and Oligo NO.20. The amplified product was also sequenced with Oligo NO.9. Thus, the G* signals of the sequence 5-CGCG*-3 in the read result were corresponding to the signals for 5fC. The reaction conditions were the same as set forth. The reaction product was directly recovered through ethanol precipitation.

Figure 9A:
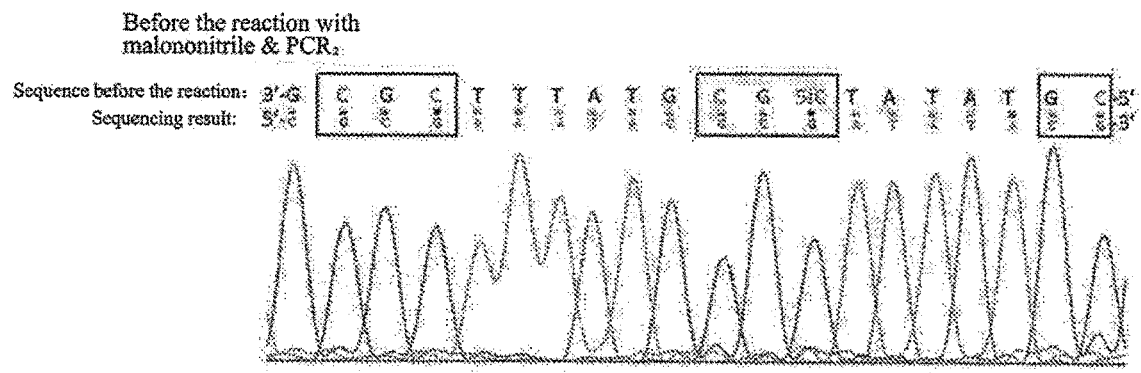
FIGS. 9A and 9B are respectively the sequencing results obtained before and after the reaction with malononitrile in example 5, which show that "ring formation promoting 5fC to T conversion sequencing technique" is implemented with compound ii of malononitrile, wherein 5fC* represents the product obtained after the reaction of 5fC."
Figure 9B:
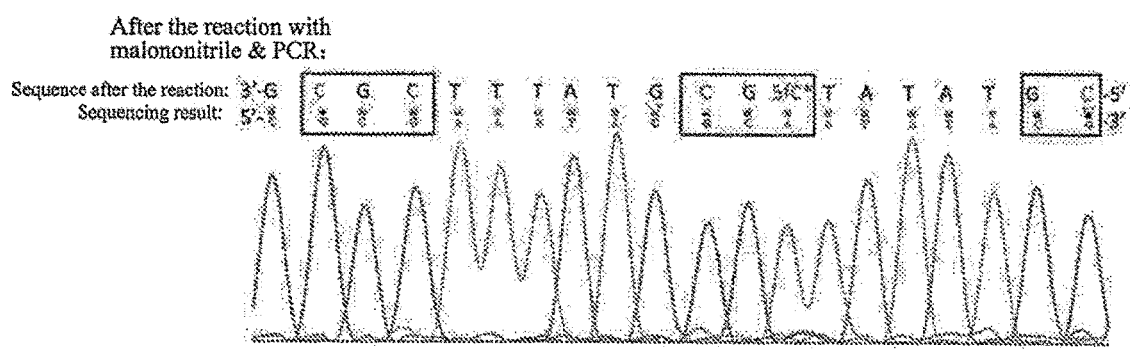

The sequences before and after the reaction were directly amplified by PCR reaction respectively. The amplified products were sequenced with reverse primer, obtaining the results as shown in FIGS. 9A and 9B. Before the reaction with malononitrile, the 5fC base position was read as guanine G signal. After the reaction, the 5fC base position was read as thymine T during PCR amplification. Thus, when using reverse sequencing primer, 5fC position was read as adenine A signal. By comparing the sequence information before and after the reaction, C-T mutation signal (forward primer sequencing) or G-A mutation signal (reverse primer sequencing) was found to be the position of 5fC base. In this way, single base resolution sequence information of 5fC in a nucleic acid sequence can further be easily detected.

In this method, 5fC was reacted with malononitrile, such that the reaction product of 5fC can also be amplified into thymine T during PCR amplification. Such 5fC sequencing methods are also classified as "ring formation promoting 5fC to T conversion sequencing technique"

Example 6

Specifical Detection of the Concentration of 5fC by Means of the Fluorescence Property of the Reaction Product of Malononitrile It was found that all the compounds i, ii, and iii can enable sample to exhibit new ultraviolet absorption peaks, when using Nanodrop micro-ultraviolet spectrophotometer from Thermo to quantify the Oligo NO.1 (-AGA TC$^5$GTAT-3) sample after reaction. As shown in FIG. 10, the reaction product of Oligo NO.1 with malononitrile exhibits a new absorption peak at about 330 nm; the reaction product of Oligo NO.1 with 1,3-indandione exhibits a new absorption peak at about 310 nm; the reaction product of Oligo NO.1 with ethyl acetoacetate or methyl acetoacetate exhibits a new absorption peak at about 350 nm; and the reaction product of Oligo NO.1 with diethyl malonate exhibits a new absorption peak at about 345 nm. Since a new ultraviolet absorption can be detected due to the formation of conjugate polycyclic derivative, the reaction product is possible to generate new fluorescence. New fluorescence of the reaction product was indeed detected by a fluorescence spectrophotometer. Here, only the reaction product of malononitrile with 5fC base is used as an example for illustration. The other aforementioned compounds containing an active methylene are not additionally discussed here.

The reaction product of malononitrile with 5fC base DNA possesses good fluorescence. As shown in FIG. 11, Oligo NO.1 was used as raw material to react with malononitrile, and the obtained reaction product was determined via a fluorescence spectrophotometer to be a new resulting product (included within the scope of compound I) with a max excitation wavelength of 328 nm and a max emission wavelength of 370 nm.

The reaction product was quantitatively prepared into standard solutions with a concentration gradient. Meanwhile, the sample solution of raw material Oligo NO.1 was prepared with the same concentration gradient. The fluorescence intensities of the two kinds of solutions with various concentration gradients were determined under the same condition. The difference between the fluorescence intensities of the two kinds of solutions was calculated by subtracting the intensity of raw material form that of the reaction product to obtain the net increase between the fluorescence intensities before and after the reaction. As shown in FIGS. 12A and 12B, with the increase of the reaction product's concentration, the net increase of fluorescence intensity increases proportionally (FIG. 12A). A standard curve was plotted with the net increase of fluorescence intensity as the vertical axis and with the corresponding concentration as the horizontal axis, exhibiting a good linear relationship. The lower limit of detection can reach 10 nM (FIG. 12B).

The fluorescence activation effect of such reaction products can be used to quantify the concentration of 5fC base, and also can be used to label the 5fC base in a nucleic acid sample.

Example 7

Influencing the Identification of a Substrate Sequence with TaqαI Endonuclease by Means of Compound AI Reaction TaqαI can cleave a double-stranded DNA containing a 5-TCGA-3 palindromic sequence, and the second base cytosine can be 5-position modified (5mC, 5hmC, 5fC, 5caC) base (Shinsuke Ito, et al., *Science,* 2011, 333:1300-1303). By means of the reactions of the aforementioned 3 kinds of compounds with the 5fC base in the 5-TC$^{5f}$GA-3 sequence, the chemical property of the 5fC base were altered, which may change the ability of TaqαI to identify a substrate sequence. Here, only the reaction product of compound AI with 5fC base is used as an example for illustration. The other aforementioned active methylene compounds are not additionally discussed here.

The used double-stranded DNA is Oligo NO.22, the forward chain of which comprises a 5-TC$^{5f}$GA-3 sequence, and the backward chain of which does not comprise any 5fC base. The reference sequence is Oligo NO.23, the sequence of which is identical to Oligo NO.22, except that it does not contain any 5fC base. Compound AI was reacted with Oligo NO.22, a biotin was coupled to Oligo NO.22 through Click Chemistry, and the completely labeled double-stranded Oligo NO.22 reaction product sequence was eluted with DTT after enrichment. Then, the reference sequence Oligo NO.23, the Oligo NO.22 before the reaction, and the reacted and eluted Oligo NO.22 sequenced were simultaneously digested with TaqαI for 1 h, and loaded to 4% agarose gel to determine whether the sequences were digested completely by electrophoresis. As 5-TC$^{5f}$GA-3 or 5-TCGA-3 is located in the middle of the used sequence of Oligo NO.22 or Oligo NO.23, the sequence size before digestion is 70 bp, and the sequence size of the completely digested product is 35 bp.

As shown in FIG. 13, in the control group, the samples containing a double-stranded 5-TCGA-3 (Oligo NO.23) or 5-TC$^{5f}$GA-3 (Oligo NO.22) can be digested completely, while in the experimental group, the sample obtained from the reaction of 5-TC5fGA-3 (Oligo NO.22) with compound AI and enrichment cannot be digested, indicating that the reaction product influences the identification of a substrate with TaqαI.

Example 8

Detection of Distribution of 5fC Base in Mouse Embryonic Stem Cell Genomic DNA by the "Ring Formation Promoting 5fC to T Conversion Sequencing Technique" Based on Compound AI To confirm whether the method of the present invention can detect distribution information of 5-formylcytosine and single-base resolution sequence information in biological samples (for example genomic DNA), the "ring formation promoting 5fC to T conversion sequencing technique" based on compound AI is used for illustration here. In particular, the above examples 3 and 4 were applied to the genomic DNA samples of mice embryonic stem cells (mESC).

The pretreated genomic DNA of wild-type mESC was reacted with compound AI for 24 hours. The DNA was recovered and coupled with a biotin group through Click reaction. The DNA sequence containing a label was separated and enriched with streptavidin magnetic beads, obtaining the DNA fragments with 5fC bases distributed therein. The obtained samples were subjected to the second generation sequencing library construction, PCR amplification, and then high-throughput sequencing. The sequencing results were aligned back with the genome. Thus the distribution information and single base resolution sequence information of 5fC bases in the mESC genome can be observed.

Figure 14:
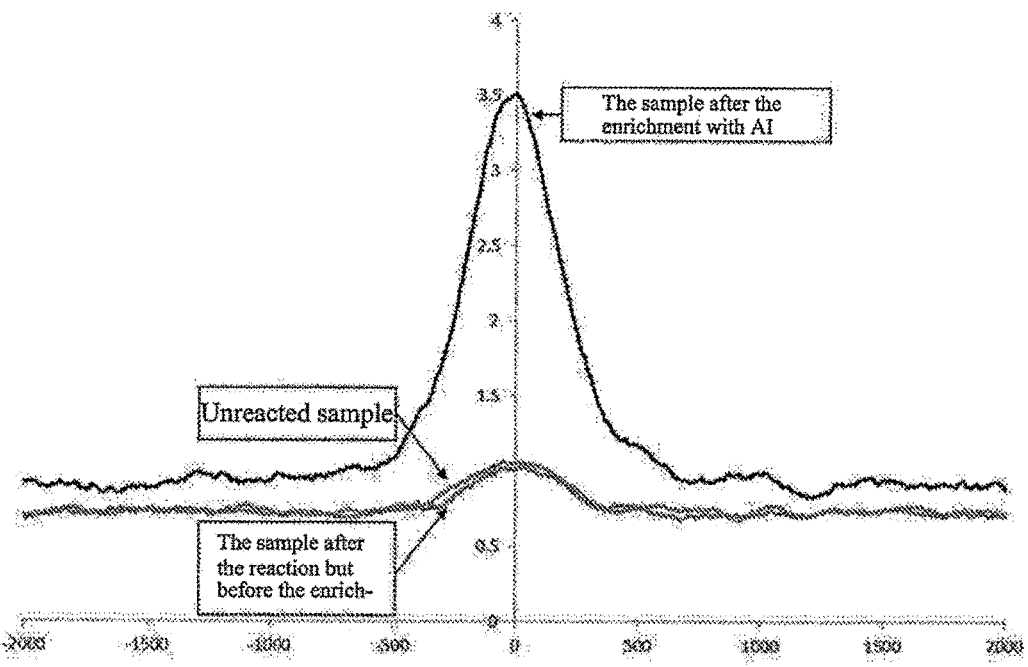
FIG. 14 shows the enrichment of 5fC distribution regions of genomic DNA in mice embryonic stein cells with compound AI in example 7.

As shown in FIG. 14, three samples of genomic DNAs were sequenced in a batch, including an unreacted sample, a sample after reaction but before enrichment, and an enriched sample. It can be seen that no significant enrichment distribution was observed for the unreacted sample and the sample before enrichment, while a significant enrichment peak in the distribution region of 5fC base was observed for the enriched sample. The results shows that, the enrichment of the 5fC base-containing DNA sequences based on compound AI is feasible, and can be used to analyze the genomic distribution information of 5fC base in combination with high-throughput sequencing data.

Figure 15:
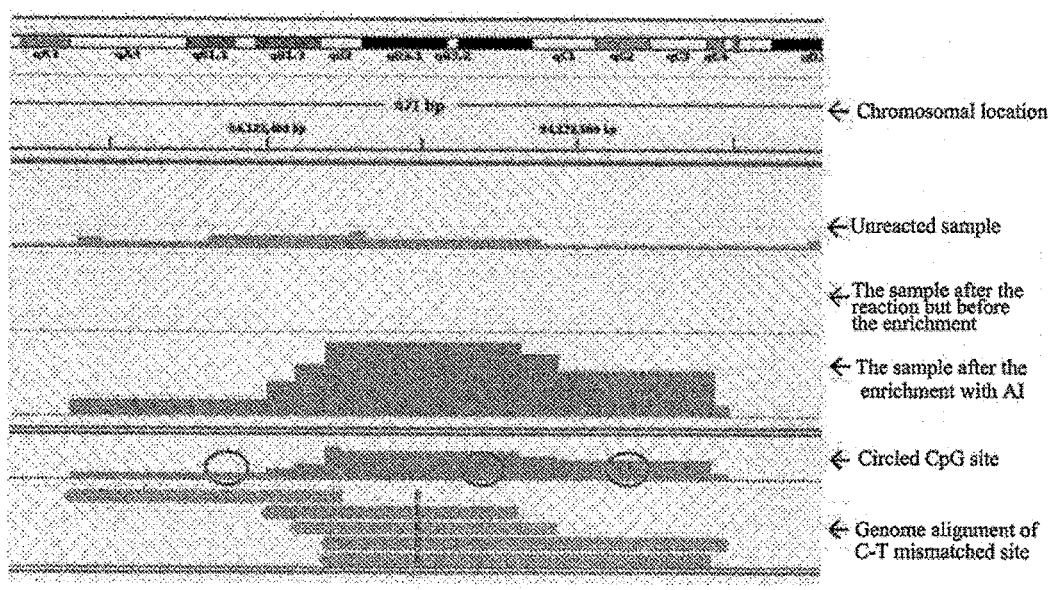
FIG. 15 shows the representative regions of 5fC single-base resolution position in the genomic DNA of mice embryonic stem cells exhibited by the "ring formation promoting 5fC to T conversion sequencing technique" based on compound AI in example 7.

In view that 5fC base was read as cytosine T during PCR amplification after the reaction with compound AI, the single-base resolution position of 5-formylcytosine can be detected through the detection of C-T mis-matched positions in the sequence read in high-throughput sequencing. FIG. 15 shows a representative position of C-T mis-match of in the enrichment peak. It can be seen that each sequence read out in the enrichment peak contains one C-T mis-matched position, and 4 C-T mis-matched positions were obtained by comparing with the genome, wherein 3 circled mis-matched positions were located at the position of CpG dyad. It follows that "ring formation promoting 5fC to T conversion sequencing technique" can detect single-base resolution position of 5fC base in real biological samples.

By combining the two methods of the above "5fC ring protecting sodium bisulfite sequencing technique" and "ring formation promoting 5fC to T conversion sequencing technique", the single-base resolution read information of all cytosines during the sequencing reading can be summarized in the table as shown in FIG. 16. In conventional sequencing, all the 5 kinds of cytosines are read as cytosine C; in conventional sodium bisulfite sequencing, 5-methylcytosine and 5-hydroxymethylcytosine are read as C, while cytosine, 5-formylcytosine and 5-carboxylcytosine are read as thymine T. In the "5fC ring protecting sodium bisulfite sequencing technique" provided in the present invention, 5fC base is protected, and is read as T in sodium bisulfite sequencing. Therefore, the position of 5fC base can be identified by comparing with the result of conventional sodium bisulfite sequencing. In addition, in the "5fC ring formation promoting sodium bisulfite sequencing technique" provided in the present invention, through direct PCR amplification and sequencing, 5fC base is read as thymine T. By comparing with the result of conventional sequencing, the C-T mis-matched position is the single-base resolution sequence position of 5fC base.

The invention claimed is:

1. A method for specific chemical labeling of 5-formylcytosine or a 1-substituted derivative thereof, comprising the step of reacting an active methylene compound containing a side-chain active group $R_1$—$CH_2$—$R_2$ with the 5-formylcytosine or a 1-substituted derivative thereof, wherein a dehydration condensation reaction occurs between the active methylene compound containing a side-chain active group and a 5-formyl group of cytosine in the 5-formylcytosine or a 1-substituted derivative thereof, and at the same time an intramolecular reaction occurs between the side-chain active group of the active methylene compound and a 4-amino group of cytosine in the 5-formylcytosine or a 1-substituted derivative thereof to implement ring closing, as shown in the equation below:

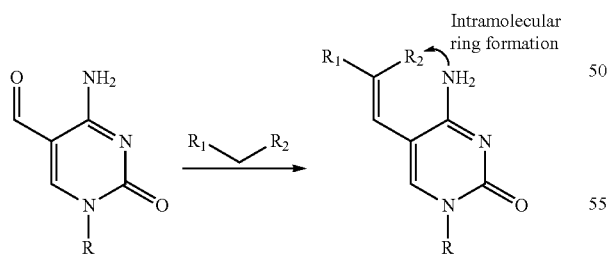

wherein, R represents hydrogen, hydrocarbyl, hydrocarbyl with —OH, —$NH_2$, —CHO and/or —COOH, ribosyl or deoxyribosyl, 5'- or 3'-phosphate-modified ribosyl or deoxyribosyl, or structures excluding the 5-formylcytosine from ribonucleic acid or deoxyribonucleic acid binding to 1-position of the 5-formylcytosine via glucosidic bond; the hydrocarbyl is C1-C30 linear or branched alkyl, C1-C30 linear or branched alkenyl, or C1-C30 linear or branched alkynyl;

$R_1$ is an electrondrawing group selected from the group consisting of cyano, nitro, formyl, carbonyl compound

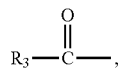

and

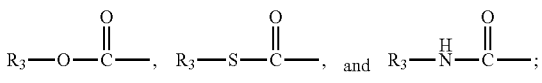

$R_2$ is an electrondrawing group selected from the group consisting of cyano, formyl, carbonyl compound

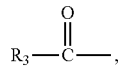

and

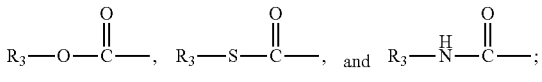

$R_3$ is an unsubstituted C1-C30 linear or branched alkyl, alkenyl or alkynyl, or a C1-C30 linear or branched alkyl, alkenyl or alkynyl substituted with —OH, —$NH_2$, —CHO, —COOH, azido and/or biotin; and $R_1$ and $R_2$ are independent from each other or forming a ring directly by bonding with each other or forming a ring indirectly by bonding via an atom C, N or O.

2. The method according to claim 1, characterized in, that the active methylene compound containing a side-chain active group is compound i as shown in formula i, and the compound i reacts with the 5-formylcytosine or a 1-substituted derivative thereof in one step to synthesize compound I as shown in formula I:

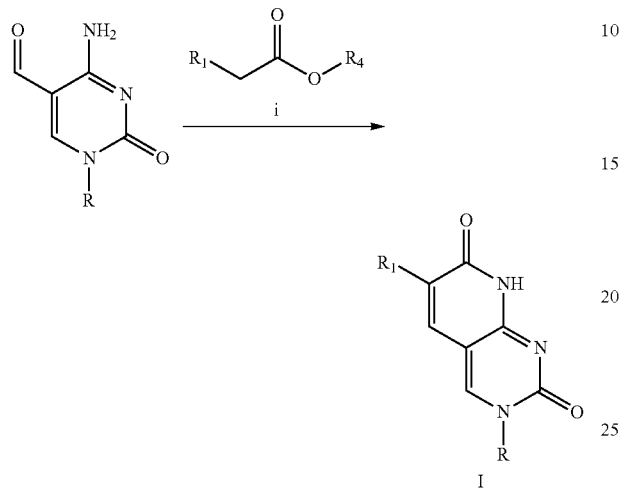

wherein R and $R_1$ are respectively as described in claim 1; $R_4$ represents C1-C30 linear or branched alkyl, alkenyl or alkynyl, or C1-C30 linear or branched alkyl substituted with —OH, —NH$_2$, —CHO and/or —COOH.

3. The method according to claim 2, characterized in, the compound i is methyl acetoacetate, ethyl acetoacetate, diethyl malonate or ethyl 6-azido-3-oxyhexanoate.

4. The method according to claim 1, characterized in that, the active methylene compound containing a side-chain active group is compound ii as shown in formula ii, and said compound ii reacts with the 5-formylcytosine or a 1-substituted derivative thereof in one step to synthesize compound II as shown in formula II:

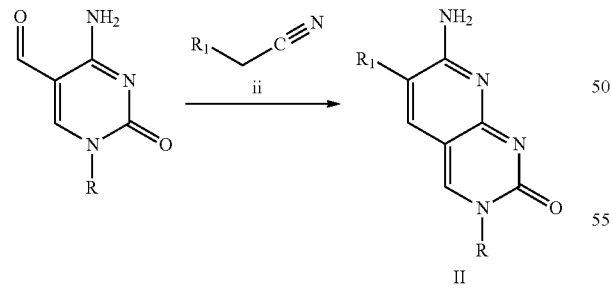

wherein R and $R_1$ are respectively as described in claim 1.

5. The method according to claim 4, characterized in, the compound ii is malononitrile.

6. The method according to claim 1, wherein the active methylene compound containing a side-chain active group is compound iii as shown in formula iii, and said compound iii reacts with the 5-formylcytosine or a 1-substituted derivative thereof in one step to synthesize compound III as shown in formula III:

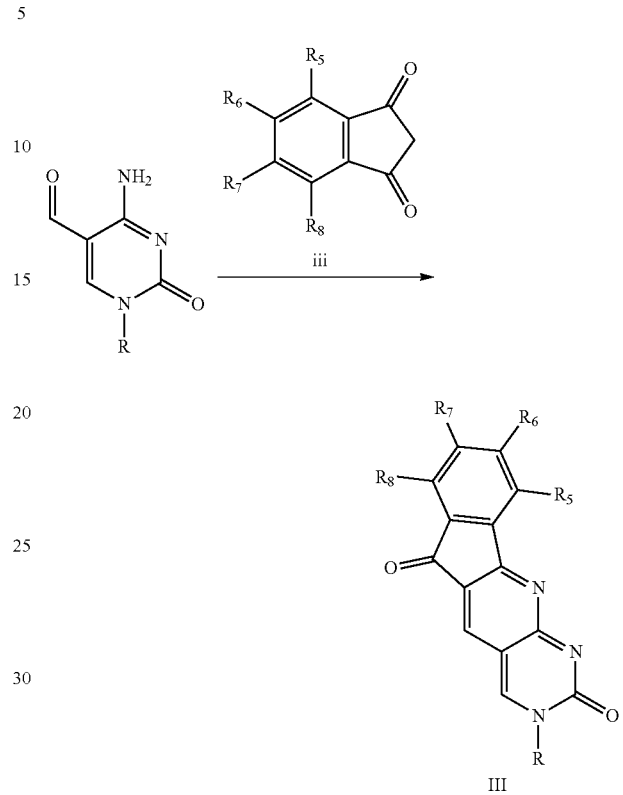

wherein R is as described in claim 1; and $R_5$, $R_6$, $R_7$ and $R_8$ are, independently from each other, hydrogen, —OH, —NH$_2$, —CHO, —COOH, —CN, —NO$_2$, azido, or C1-C30 linear or branched alkyl, alkenyl or alkynyl, or C1-C30 linear or branched alkyl, alkenyl or alkynyl substituted with —OH, —O—, —NH$_2$, —NH—, —CHO, —COOH, azido and/or biotin;

or the active methylene compound containing a side-chain active group is a compound as shown in formula iv,

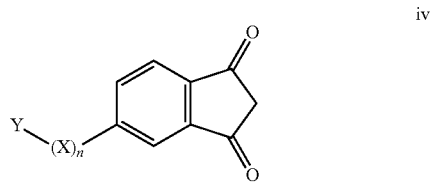

in formula iv, X represents C1-C5 linear or branched hydrocarbyl, or C1-C5 linear or branched hydrocarbyl with ether bond —O— and/or imino group —NH—; n is a positive integer greater than or equal to 1; and Y is biotin, azido, or C2-C20 alkynyl.

7. A compound selected from the compound as shown in formula I, II, III or iv:

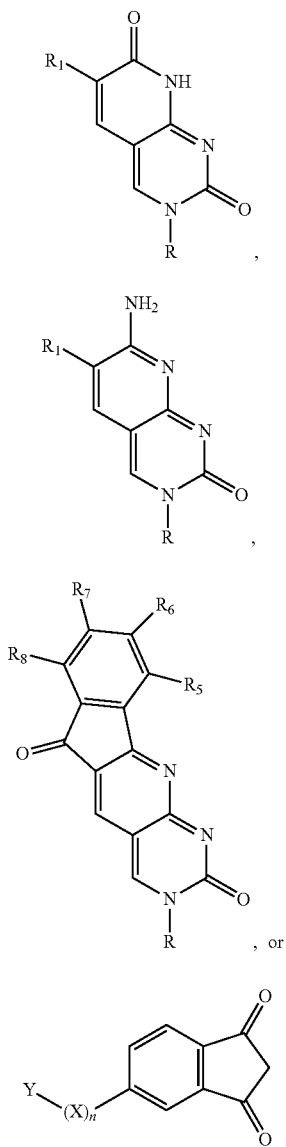

wherein, R and $R_1$ are as defined in claim 1; $R_5$, $R_6$, $R_7$ and $R_8$ are, independently from each other, hydrogen, —OH, —$NH_2$, —CHO, —COOH, —CN, —$NO_2$, azido, or C1-C30 linear or branched alkyl, alkenyl or alkynyl, or C1-C30 linear or branched alkyl, alkenyl or alkynyl substituted with —OH, —O—, —$NH_2$, —NH—, —CHO, —COOH, azido and/or biotin; X represents C1-C5 linear or branched hydrocarbyl, or C1-C5 linear or branched hydrocarbyl with ether bond —O— or imino group —NH—; n is a positive integer greater than or equal to 1; and Y is biotin, azido, or C2-C20 alkynyl.

8. The method according to claim 1, wherein the hydrocarbyl is C1-C10 linear or branched alkyl, C1-C10 linear or branched alkenyl, or C1-C10 linear or branched alkynyl.

9. The method according to claim 1, wherein R represents —$CH_3$, —$CH_2CH_3$, —CHO, —$CH_2CHO$ or

—C(=O)$CH_3$.

10. The method according to claim 2, characterized in that, $R_4$ represents C1-C10 linear or branched alkyl or C1-C10 linear or branched alkyl substituted with —OH, —$NH_2$, —CHO and/or —COOH.

11. The method according to claim 6, wherein $R_5$, $R_6$, $R_7$ and $R_8$ are, independently from each other, hydrogen, —OH, —$NH_2$, —CHO, —COOH, —CN, —$NO_2$, azido, or C1-C10 linear alkyl, or C1-C10 linear alkyl substituted with —OH, —O—, —$NH_2$, —NH—, —CHO, —COOH, azido and/or biotin;

X is —$CH_2$—, —O—$CH_2$—$CH_2$—, —$CH_2$—O—$CH_2$— or —$CH_2$—$CH_2$—O—;

n is a positive integer between 1 and 9; and

Y is biotin, azido, or ethynyl or cyclooctynyl.

12. The method according to claim 6, wherein X is —$CH_2$—, n is a positive integer between 1 and 9, and Y is biotin, azido or ethynyl.

13. The method according to claim 6, wherein the compound iii is 1,3-indandione; or the compound as shown in formula iv is 5-(2-azidoethyl)-1,3-indandione.

14. The compound according to claim 7, wherein in formula III, $R_5$, $R_6$, $R_7$ and $R_8$ are, independently from each other, hydrogen, —OH, —$NH_2$, —CHO, —COOH, —CN, —$NO_2$, azido or C1-C10 linear alkyl, or C1-C10 linear alkyl substituted with —OH, —O—, —$NH_2$, —NH—, —CHO, —COOH, azido and/or biotin; and in formula iv, X is —$CH_2$—, —O—$CH_2$—$CH_2$—, —$CH_2$—O—$CH_2$— or —$CH_2$—$CH_2$—O—, n is a positive integer between 1 and 9, and Y is biotin, azido, or ethynyl or cyclooctynyl.

15. The compound according to claim 7, characterized in that, in formula iv, X is —$CH_2$—, n is a positive integer between 1 and 9, and Y is biotin, azido or ethynyl.

16. The compound according to claim 7, wherein it is a compound selected from the compounds of the following formulas:

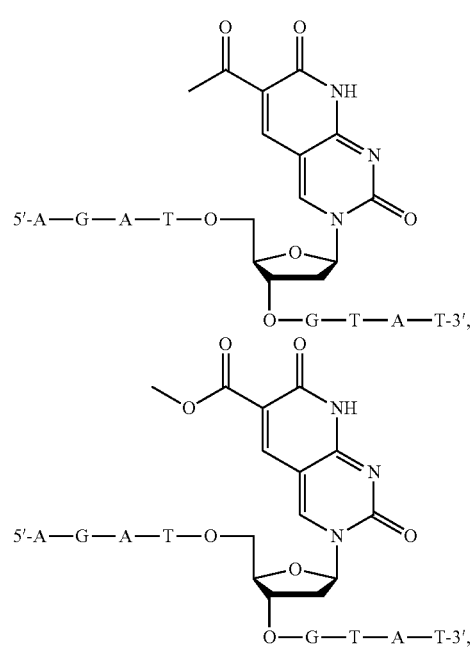

-continued

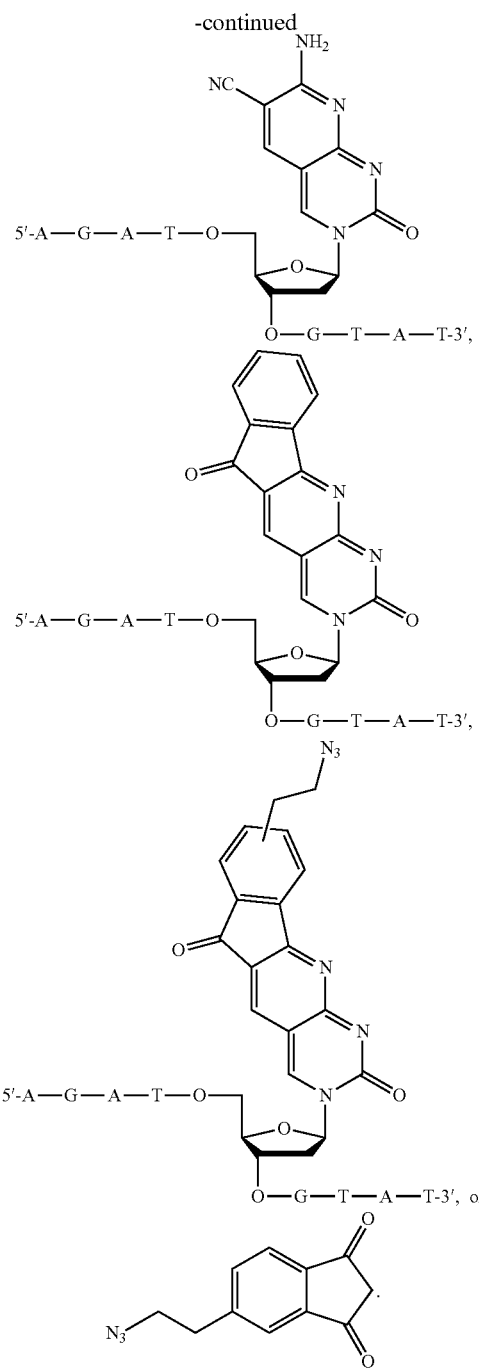

17. A kit for detecting 5-formylcytosine base, comprising the active methylene compound containing a side-chain active group R$_1$—CH$_2$—R$_2$ as defined in claim 1, and corresponding reaction solvent, wherein the corresponding reaction solvent is an alkaline organic solution or an acidic to neutral aqueous solution.

18. The kit according to claim 17, wherein the active methylene compound containing a side-chain active group R$_1$—CH$_2$—R$_2$ is the compound i as defined in claim 2, the compound ii as defined in claim 4, or the compound iii or iv as defined in claim 6.

19. The kit according to claim 17, wherein the active methylene compound containing a side-chain active group R$_1$—CH$_2$—R$_2$ is methyl acetoacetate, ethyl acetoacetate, diethyl malonate, ethyl 6-azido-3-oxyhexanoate, malononitrile, 1,3-indandione or 5-(2-azidoethyl)-1,3-indandione.

20. The kit according to claim 17, wherein it is a kit selected from:
Kit 1, comprising the following 4 modules:
Module 1: a 5-formylcytosine reaction module, comprising ethyl 6-azido-3-oxyhexanoate, and corresponding reaction solution, wherein the corresponding reaction solution is an alkaline organic solution;
Module 2: a selective enrichment module, comprising magnetic beads specifically binding to biotin, a screening buffer, and a reagent which selectively reacts with azido and contains biotin modification;
Module 3: a sodium bisulfite treatment module, comprising a sodium bisulfite treating reagent and related recovering materials; and
Module 4: a specific PCR amplification module, comprising a specific DNA polymerase and a reaction system screened for the reaction product of 5-formylcytosine;
Kit 2, comprising the following 3 modules:
Module 1: a 5-formylcytosine reaction module, comprising 5-(2-azidoethyl)-1,3-indandione, and corresponding reaction solution, wherein the corresponding reaction solution is an alkaline organic solution or an acidic to neutral aqueous solution;
Module 2: a selective enrichment module, comprising magnetic beads specifically binding to biotin, a screening buffer, and a reagent which selectively reacts with azido and contains biotin modification; and
Module 3: a specific PCR amplification module, comprising a specific DNA polymerase and a reaction system screened for the reaction product of 5-formylcytosine;
Kit 3, comprising the following 3 modules:
Module 1: a module for immunoprecipitation enrichment of 5-formylcytosine, comprising a 5 formylcytosine antibody and corresponding reaction buffer for DNA immunoprecipitation test;
Module 2: a 5-formylcytosine reaction module, comprising malononitrile or 1,3-indandione, and corresponding reaction solution, wherein, for malononitrile, the corresponding reaction solution is an acidic to neutral aqueous solution; and for 1,3-indandione, the corresponding reaction solution is an alkaline organic solution or an acidic to neutral aqueous solution; and
Module 3: a specific PCR amplification module, comprising a specific DNA polymerase and reaction system screened for the reaction product of 5-formylcytosine; and
Kit 4, comprising the following 2 modules:
Module 1: a 5-formylcytosine reaction module, comprising ethyl 6-azido-3-oxyhexanoate or 5-(2-azidoethyl)-1,3-indandione, and corresponding reaction solution, wherein, for ethyl 6-azido-3-oxyhexanoate, the corresponding reaction solution is an alkaline organic solution; and for 5-(2-azidoethyl)-1,3-indandione, the corresponding reaction solution is an alkaline organic solution or an acidic to neutral aqueous solution; and
Module 2: a selective enrichment module, comprising magnetic beads specifically binding to biotin, a screening buffer, and a reagent which selectively reacts with azido and contains biotin modification.

* * * * *